(12) United States Patent
Brimer et al.

(10) Patent No.: US 9,706,946 B2
(45) Date of Patent: Jul. 18, 2017

(54) SPIROMETER SYSTEM AND METHODS OF DATA ANALYSIS

(71) Applicant: SPARO INC., St. Louis, MO (US)

(72) Inventors: Andrew Brimer, St. Louis, MO (US); Abigail Cohen, Huntington Woods, MI (US); Braden Eliason, Shoreview, MN (US); Olga Neyman, Duluth, GA (US)

(73) Assignee: SPARO INC., St. Louis, MO (US)

( * ) Notice: Subject to any disclaimer, the term of this patent is extended or adjusted under 35 U.S.C. 154(b) by 898 days.

(21) Appl. No.: 13/900,253

(22) Filed: May 22, 2013

(65) Prior Publication Data

US 2013/0317379 A1 Nov. 28, 2013

Related U.S. Application Data

(60) Provisional application No. 61/650,122, filed on May 22, 2012, provisional application No. 61/732,065, filed on Nov. 30, 2012.

(51) Int. Cl.
*A61B 5/08* (2006.01)
*A61B 5/087* (2006.01)
(Continued)

(52) U.S. Cl.
CPC ............ *A61B 5/087* (2013.01); *A61B 5/0022* (2013.01); *A61B 5/097* (2013.01); *A61B 5/7275* (2013.01); *G01F 1/3227* (2013.01); *G01F 1/3245* (2013.01); *G06F 19/3481* (2013.01); *A61B 5/0205* (2013.01); *A61B 5/1118* (2013.01); *A61B 5/6898* (2013.01);
(Continued)

(58) Field of Classification Search
CPC ..... A61B 5/087; A61B 5/0022; A61B 5/7275; A61B 5/097; A61B 2560/0242; A61B 5/7203; A61B 2560/0443; A61B 2505/09; A61B 5/7253; A61B 5/0205; A61B 5/1118; G01F 1/3245; G01F 1/3227; G06F 19/3481
See application file for complete search history.

(56) References Cited

U.S. PATENT DOCUMENTS 3,690,171 A 9/1972 Tippetts et al.
4,244,230 A 1/1981 Bauer
(Continued)

FOREIGN PATENT DOCUMENTS

| DE | 10119860 A1 | 10/2002 |
|---|---|---|
| WO | 2012038903 A2 | 3/2012 |
| WO | WO-2013177300 A1 | 11/2013 |

OTHER PUBLICATIONS

Chinese Patent Application No. 2013800390078 Office Action issued Feb. 1, 2016.
(Continued)

*Primary Examiner* — Tiffany Weston
(74) *Attorney, Agent, or Firm* — Wilson Sonsini Goodrich & Rosati

(57) ABSTRACT

The present disclosure relates to an electronic spirometer that empowers users to quantitatively track and proactively manage respiratory diseases via simple integration with mobile devices, tablets, and computers. In one aspect, patients will be able to connect with their doctors to determine medication dosage and efficacy, avoid environmental triggers, and prevent attacks and exacerbations.

18 Claims, 16 Drawing Sheets

(51) Int. Cl.
*A61B 5/097* (2006.01)
*G01F 1/32* (2006.01)
*G06F 19/00* (2011.01)
*A61B 5/00* (2006.01)
*A61B 5/0205* (2006.01)
*A61B 5/11* (2006.01)

(52) U.S. Cl.
CPC ........... *A61B 5/7203* (2013.01); *A61B 5/7253* (2013.01); *A61B 5/7465* (2013.01); *A61B 2505/09* (2013.01); *A61B 2560/0242* (2013.01); *A61B 2560/0443* (2013.01); *A61B 2562/06* (2013.01)

(56) References Cited

U.S. PATENT DOCUMENTS

| | | | |
|---|---|---|---|
| 4,296,756 A | 10/1981 | Dunning et al. | |
| 4,838,091 A | 6/1989 | Markland et al. | |
| 4,843,889 A | 7/1989 | Mansy et al. | |
| 5,022,406 A | 6/1991 | Tomlinson | |
| 5,063,786 A | 11/1991 | Sanderson et al. | |
| 5,357,975 A | 10/1994 | Kraemer et al. | |
| 5,363,704 A | 11/1994 | Huang | |
| 5,396,808 A | 3/1995 | Huang et al. | |
| 5,396,809 A | 3/1995 | Huang | |
| 5,549,117 A | 8/1996 | Tacklind et al. | |
| 5,626,144 A | 5/1997 | Tacklind et al. | |
| 5,638,867 A | 6/1997 | Huang | |
| 5,704,366 A | 1/1998 | Tacklind et al. | |
| 6,168,568 B1 | 1/2001 | Gavriely | |
| 6,241,683 B1 | 6/2001 | Macklem et al. | |
| 6,261,238 B1 | 7/2001 | Gavriely | |
| 6,508,772 B2 | 1/2003 | Vilozni | |
| 6,553,844 B2 | 4/2003 | Drzewiecki | |
| 6,733,464 B2 | 5/2004 | Olbrich et al. | |
| 6,860,157 B1 | 3/2005 | Yang et al. | |
| 7,033,323 B2 | 4/2006 | Botbol et al. | |
| 7,077,810 B2 | 7/2006 | Lange et al. | |
| 7,094,208 B2 | 8/2006 | Williams et al. | |
| 7,267,652 B2 | 9/2007 | Coyle et al. | |
| 7,383,740 B2 | 6/2008 | Krasilchikov et al. | |
| 7,529,670 B1 | 5/2009 | Michaelis | |
| 7,761,302 B2 | 7/2010 | Woodcock et al. | |
| 7,785,262 B2 | 8/2010 | Melker et al. | |
| 7,827,870 B2 | 11/2010 | Cottam et al. | |
| 8,091,434 B2 | 1/2012 | Vaidya | |
| 8,136,413 B2 | 3/2012 | Sanderson | |
| 8,187,201 B2 | 5/2012 | Lynn | |
| 8,376,954 B2 | 2/2013 | Lange et al. | |
| 8,425,428 B2 | 4/2013 | Wood | |
| 2001/0003144 A1 | 6/2001 | Vilozni | |
| 2004/0039295 A1 | 2/2004 | Olbrich et al. | |
| 2004/0249301 A1 | 12/2004 | Stenqvist | |
| 2005/0119586 A1 | 6/2005 | Coyle et al. | |
| 2005/0182337 A1 | 8/2005 | Botbol et al. | |
| 2006/0100537 A1 | 5/2006 | Williams et al. | |
| 2007/0239058 A1* | 10/2007 | Krasilchikov | A61B 5/087 600/538 |
| 2008/0082018 A1 | 4/2008 | Sackner et al. | |
| 2008/0167568 A1 | 7/2008 | Rohde et al. | |
| 2008/0294060 A1 | 11/2008 | Haro et al. | |
| 2009/0112114 A1 | 4/2009 | Ayyagari et al. | |
| 2009/0253994 A1 | 10/2009 | Schuessler et al. | |
| 2010/0081902 A1 | 4/2010 | McKenna et al. | |
| 2010/0139414 A1 | 6/2010 | Sanderson | |
| 2010/0204602 A1 | 8/2010 | Addington et al. | |
| 2011/0077545 A1 | 3/2011 | Eichler | |
| 2011/0125045 A1 | 5/2011 | Scholz et al. | |
| 2011/0301485 A1 | 12/2011 | Fu et al. | |
| 2012/0022388 A1 | 1/2012 | Pittman et al. | |
| 2012/0029376 A1* | 2/2012 | Meng | A61B 5/087 600/538 |
| 2012/0041279 A1 | 2/2012 | Freeman et al. | |
| 2012/0053482 A1 | 3/2012 | Addington et al. | |
| 2012/0190999 A1 | 7/2012 | Addington et al. | |
| 2012/0302909 A1 | 11/2012 | Mayse et al. | |
| 2013/0018274 A1 | 1/2013 | O'Neill | |
| 2013/0109932 A1 | 5/2013 | Saadat et al. | |

OTHER PUBLICATIONS

European Patent Application No. 13793585.4 Extended European Search Report dated Jun. 7, 2016.
PCT Patent Application No. PCT/US2013/042260 International Preliminary Report on Patentability issued Nov. 25, 2014.
PCT/US2013/042260 International Search Report and Written Opinion mailed Aug. 15, 2013 (11 pages).
"Statement regarding possible dispute about inventorship"; Mar. 27, 2014; (1 page).
Australia Patent Application No. 2013266376 Patent Examination report No. 1 dated Nov. 5, 2016.
Chinese Patent Application No. 2013800390078 Second Office Action dated Oct. 23, 2016.

* cited by examiner

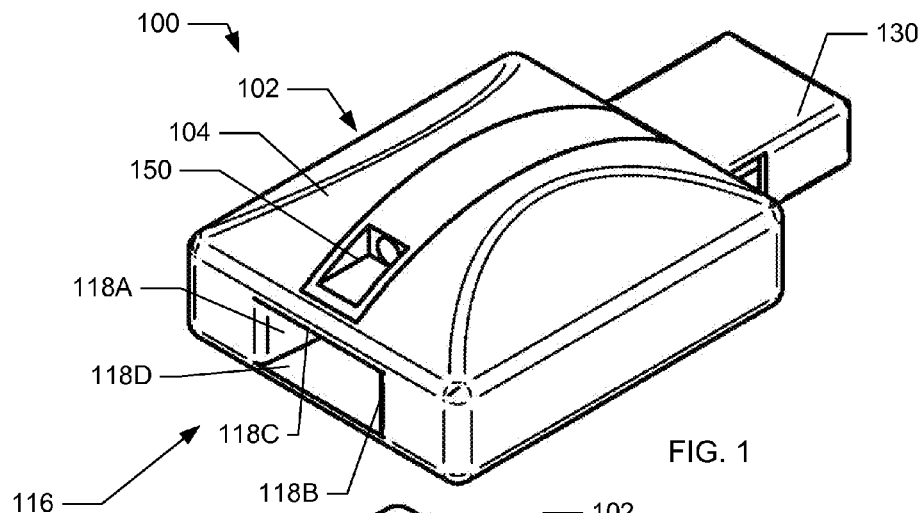
FIG. 1
FIG. 2
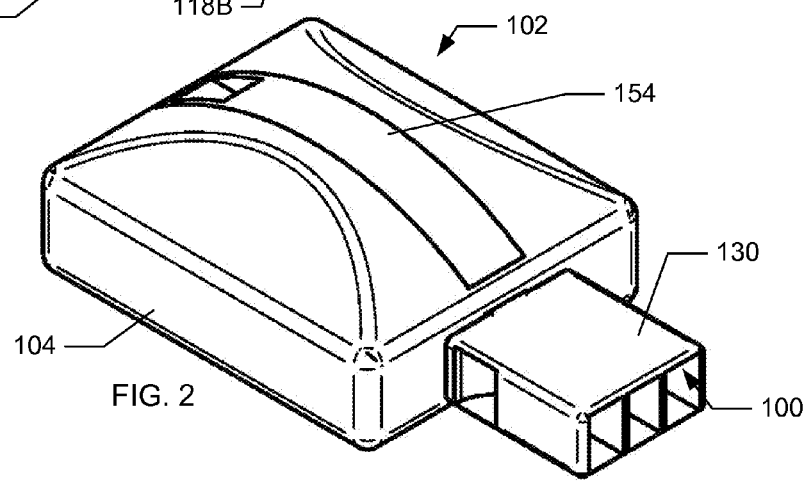
FIG. 3
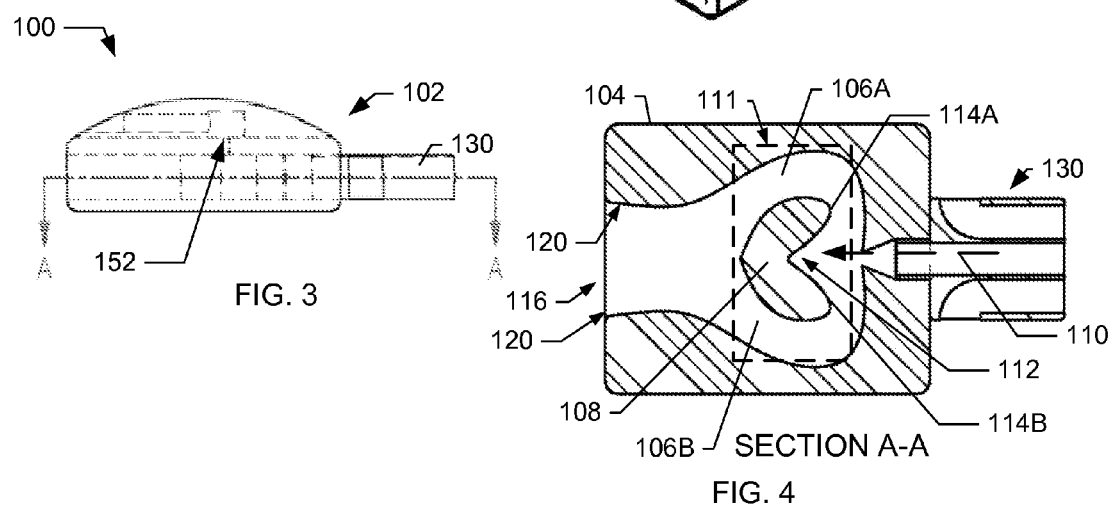
SECTION A-A
FIG. 4

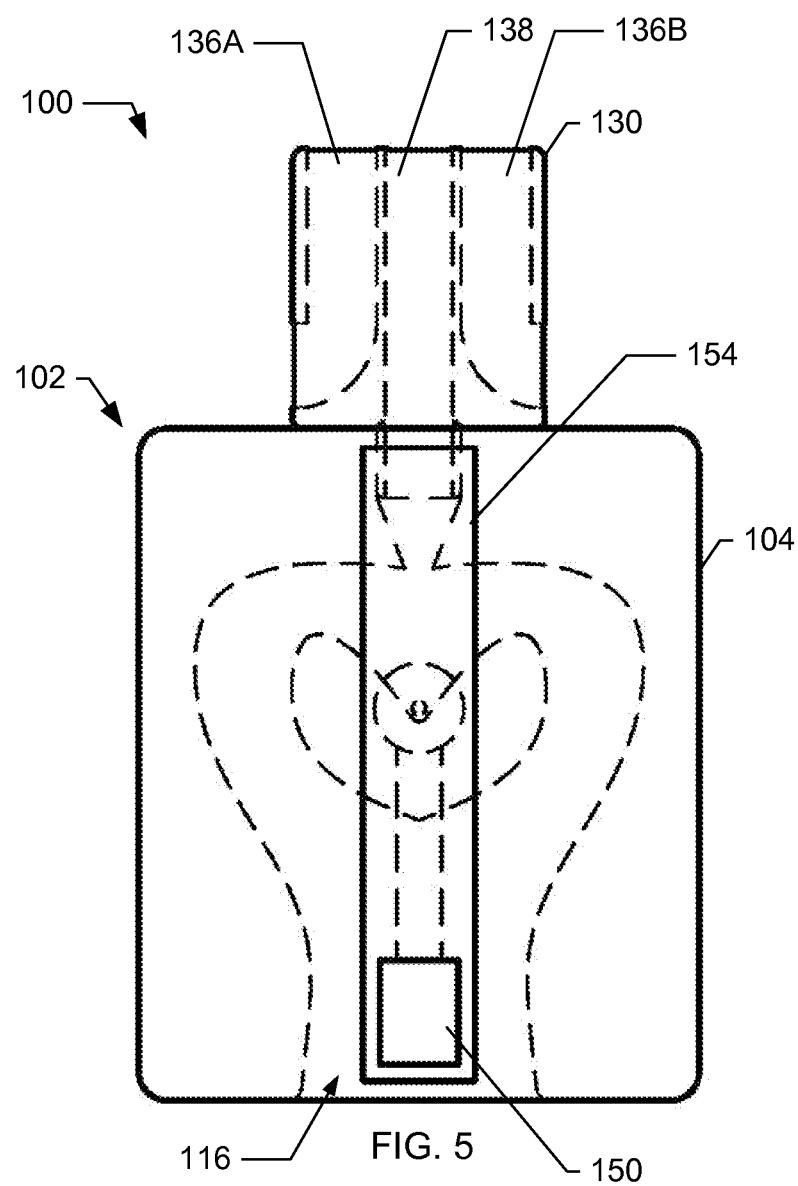
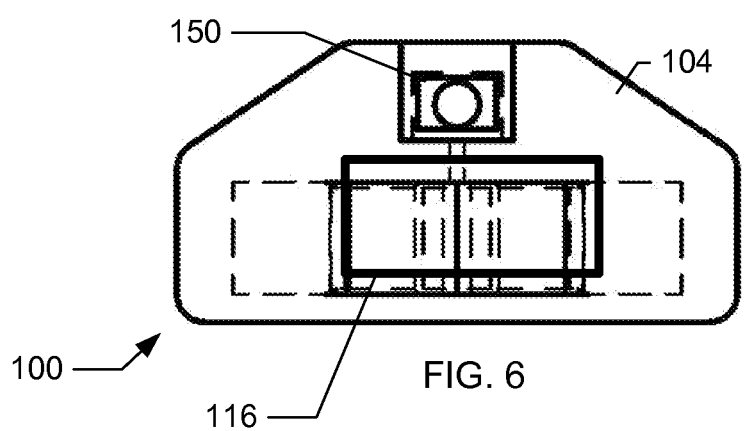

SECTION B-B

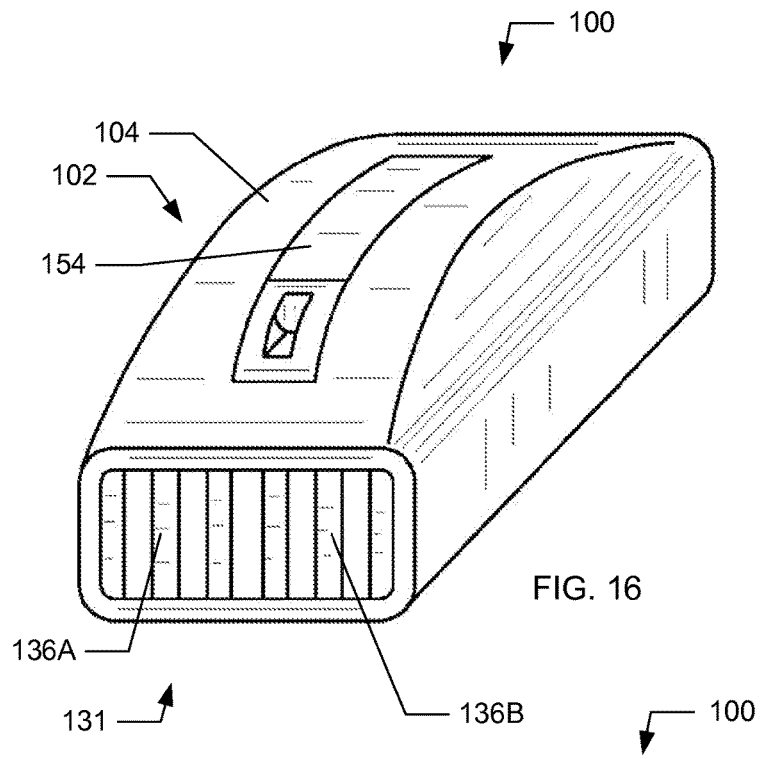
FIG. 16
FIG. 17
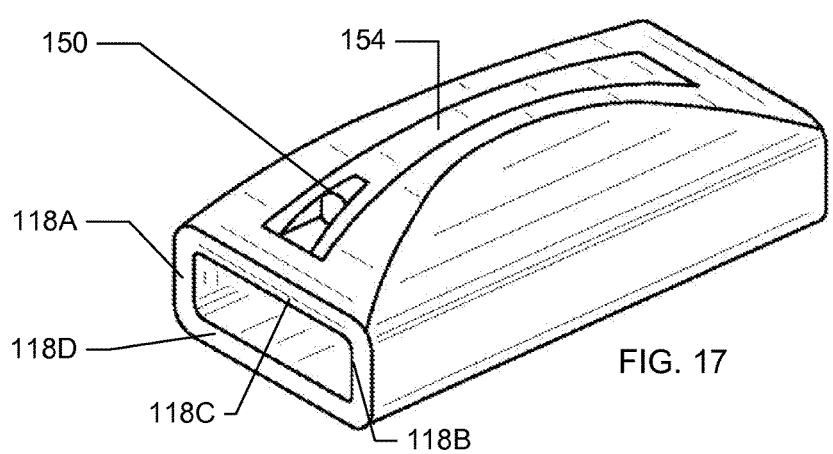
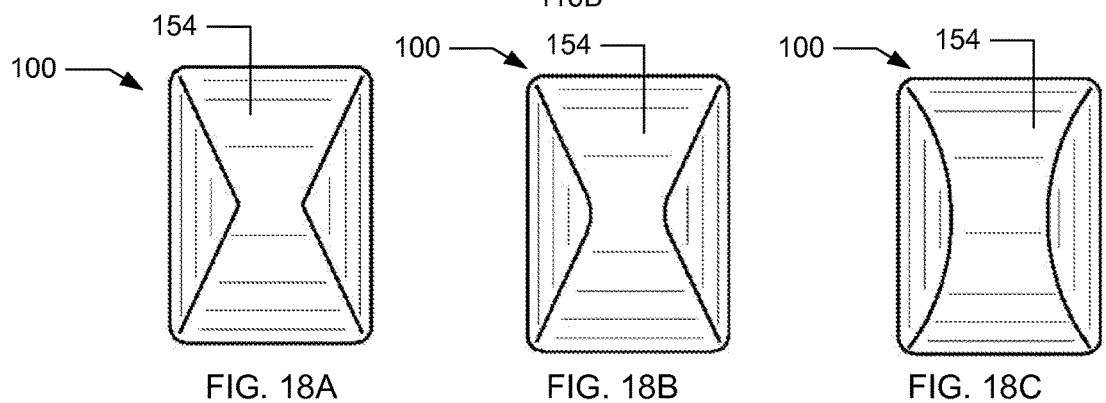
FIG. 18A  FIG. 18B  FIG. 18C

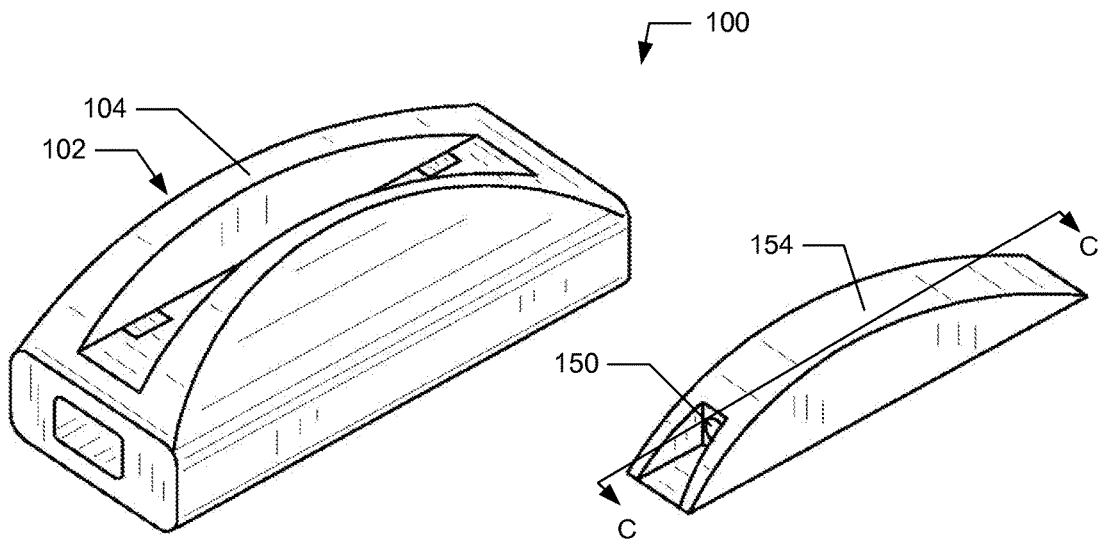
FIG. 19       FIG. 20
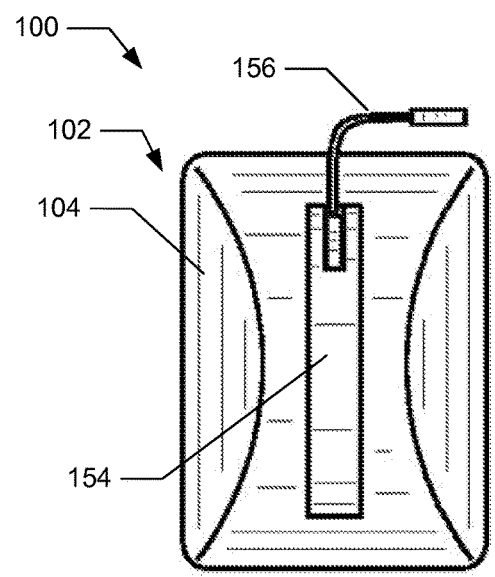
FIG. 22
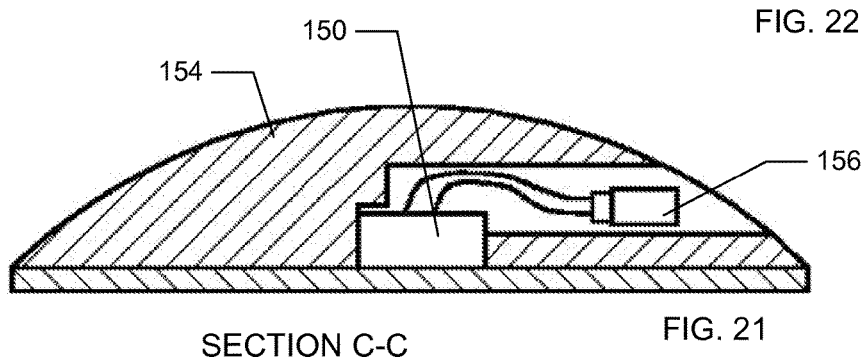
SECTION C-C       FIG. 21

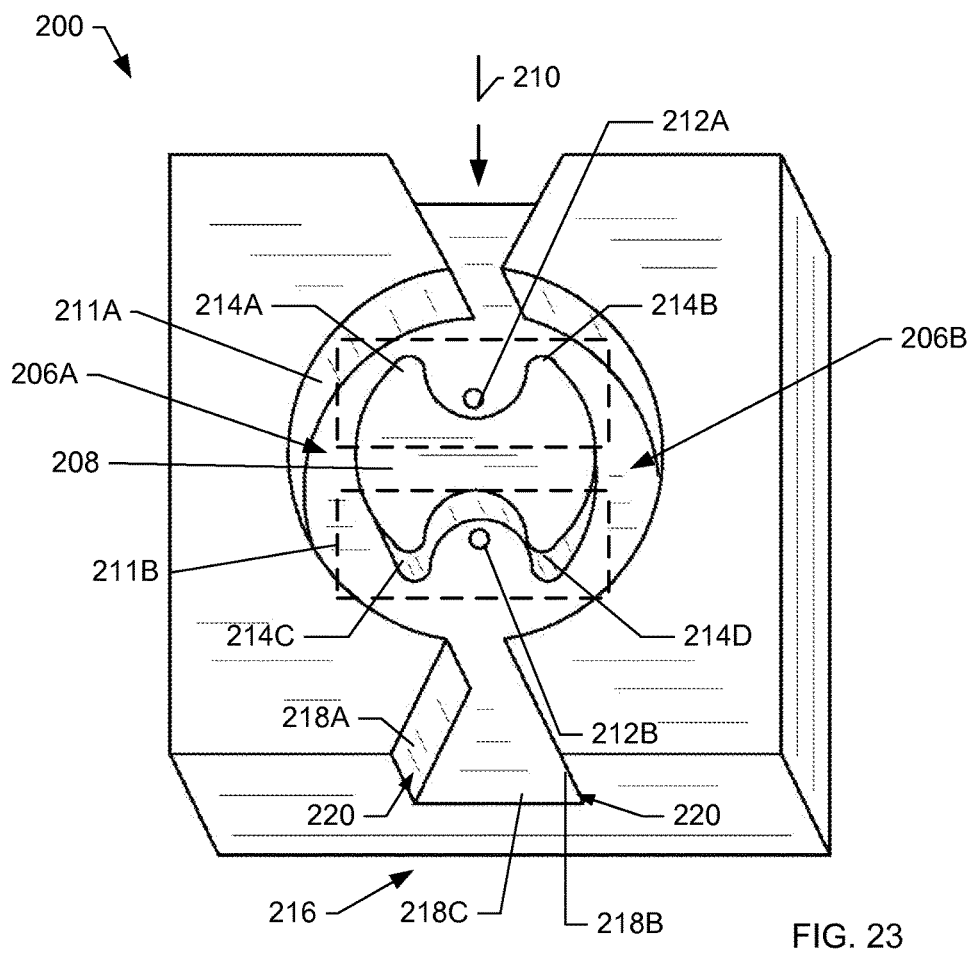
FIG. 23
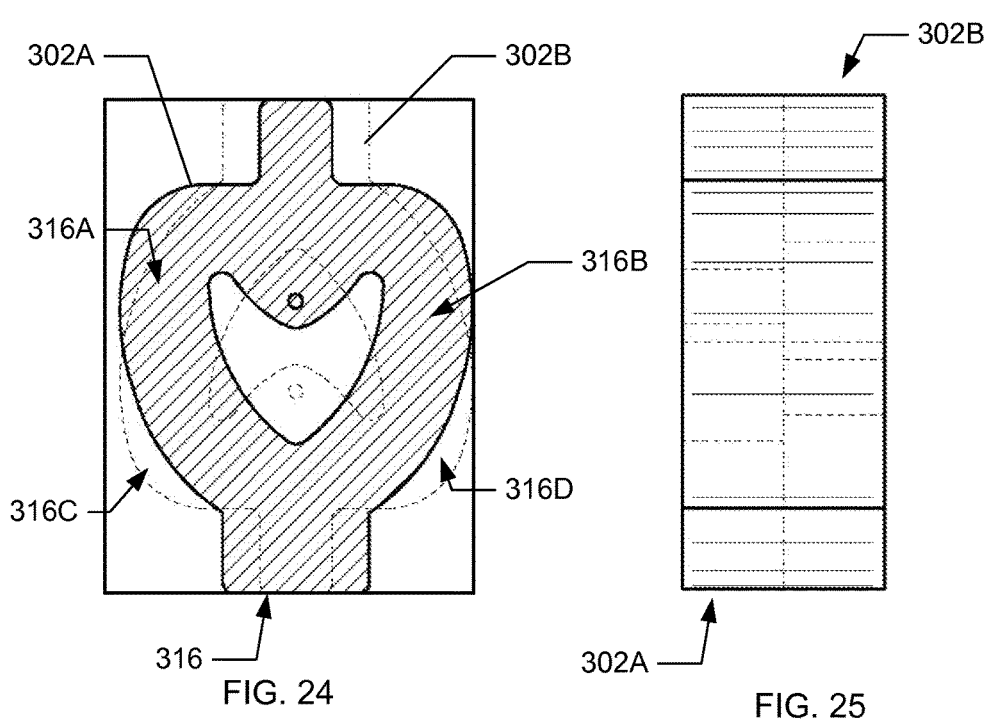
FIG. 24
FIG. 25

SPIROMETER SYSTEM AND METHODS OF DATA ANALYSIS

CROSS-REFERENCE TO RELATED APPLICATIONS

The present application claims the benefit of and priority to U.S. Provisional Patent Application No. 61/650,122, filed May 22, 2012, entitled "Spirometer and Methods of Data Analysis," and to U.S. Provisional Patent Application No. 61/732,065, filed Nov. 30, 2012, and entitled "Spirometer," the contents both applications are incorporated herein, in their entireties, by reference.

FEDERALLY SPONSORED RESEARCH OR DEVELOPMENT

Not Applicable.

COMPACT DISK APPENDIX

Not Applicable.

FIELD OF THE DISCLOSURE

The present invention related generally to a spirometer. More specifically, the present invention relates to a handheld spirometer having a fluidic oscillator.

BRIEF SUMMARY

The present disclosure relates to systems and methods for measuring airflow, which may be used to monitor or assess respiratory function. In various embodiments, the system includes a flow meter, such as a spirometer in communication with a computing device executing one or more applications to process and analyze data generated at the spirometer.

In one embodiment, a device for measuring a continuous flow rate of an airstream includes a nozzle having at least one channel to vent a portion of the airstream into an environment external to the device and at least one other channel to direct another portion of the airstream into a fluidic oscillator. The device also includes a fluidic oscillator having a housing and at least one obstacle to induce oscillations in the airstream. A frequency of the oscillations correlates to the continuous flow rate of the airstream. The device also includes at least one sensor to measure the oscillations of the airstream. The at least one sensor also generates an electronic signal corresponding to the oscillations measured and transmits the electronic signal to a computing device.

In another embodiment, a device for measuring a continuous flow rate of an air stream includes a nozzle to direct a portion of the airstream into a fluidic oscillator. The device also includes a detachable mouthpiece to reduce back pressure within the device. The detachable mouthpiece has a diameter equal to the diameter of the nozzle and defines a plurality of channels. At least one of the plurality of channels directs a portion of the airstream to the nozzle while, at least one other channel vents another portion of the airstream to an environment external to the device. The device also includes a fluidic oscillator having a housing and at least one obstacle to induce oscillations in the airstream. A frequency of the oscillations correlates to the continuous flow rate of the airstream. The device also includes at least one sensor to measure the oscillations of the airstream. The at least one sensor also generates an electronic signal corresponding to the oscillations measured and transmits the electronic signal to a computing device.

A flow meter system for monitoring lung function of a user includes an oscillation chamber to induce at least one oscillation in an airflow traversing the oscillation chamber. The airflow is generated by the user during a respiratory test. The system also includes at least one sensor to measure the rate of oscillation in the oscillation chamber and transmit a data signal to a computing device. The computing device has at least one processor and receives the data signal. The computing device also processes the data signal to determine at least one of a flow rate, time duration, or a volume of the airflow in the oscillation chamber. The system further includes a display device in communication with the computing device to display an assessment of respiratory health and a risk level to the user.

A system for monitoring lung function of a user includes at least one processor, at least one data storage device and an application executing on the at least one processor to determine spirometric characteristics of a data signal received from a spirometer. The data signal is generated in response to at least one oscillation of an airflow in the spirometer. The system also generates at least one display on a display device to display the spirometric characteristics and generates at least one risk level assessment.

The present disclosure also relates to various methods for measuring airflow and monitoring lung function. The methods may be performed using various embodiments of the devices and systems disclosed herein. The methods may also be performed with other suitable devices and systems.

BRIEF DESCRIPTION OF THE DRAWINGS

FIG. 1 is a perspective view of a first end of a spirometer device according to one embodiment.

FIG. 2 is a perspective view of a second end of the spirometer device according to one embodiment.

FIG. 3 is a side plan view of the spirometer device according to one embodiment.

FIG. 4 is a cross-sectional view of the spirometer device of FIG. 3, taken along line A-A, according to one embodiment.

FIG. 5 is a top plan view of the spirometer device according to one embodiment.

FIG. 6 is a plan view of the first end of the spirometer device according to one embodiment.

FIG. 16 is a perspective view of a first end of a spirometer device having an integrated mouthpiece according to one embodiment.

FIG. 17 is a perspective view of a second end of a spirometer device having an integrated mouthpiece according to one embodiment.

FIGS. 18A-C are top plan views of other embodiments of the spirometer device.

FIG. 19 is a perspective view of a spirometer device disengaged from a modular sensor housing according to one embodiment.

FIG. 20 is a perspective view of a modular sensor housing according to one embodiment.

FIG. 21 is a cross-sectional view of the modular sensor housing of FIG. 17 taken along the line C-C, according to one embodiment.

FIG. 22 is a top plan view of a spirometer device engaged with a modular sensor housing according to one embodiment.

FIG. 23 is a perspective view of a bi-directional spirometer device according to one embodiment.

FIG. 24 is a top plan view of a stacked bi-directional spirometer device according to one embodiment.

FIG. 25 is a side plan view of the stacked bi-directional spirometer device of FIG. 24, according to one embodiment.

DETAILED DESCRIPTION

Figure 7:
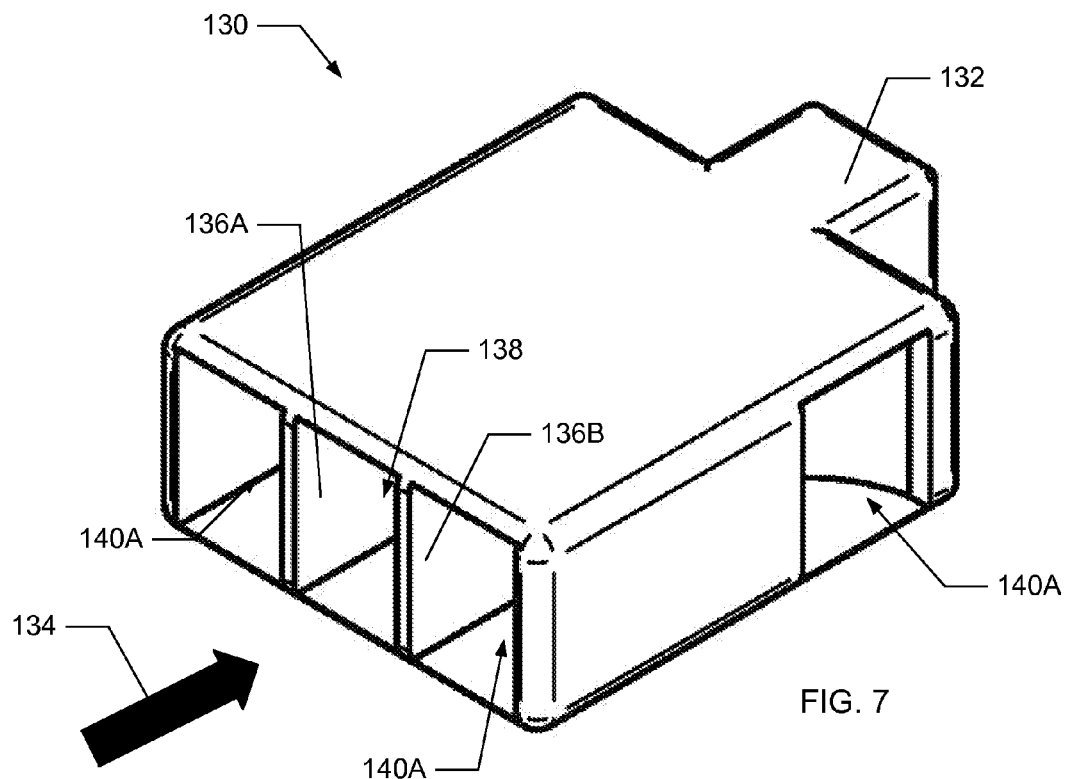
FIG. 7 is a perspective view of a first end of a spirometer mouthpiece according to one embodiment.
Figure 8:
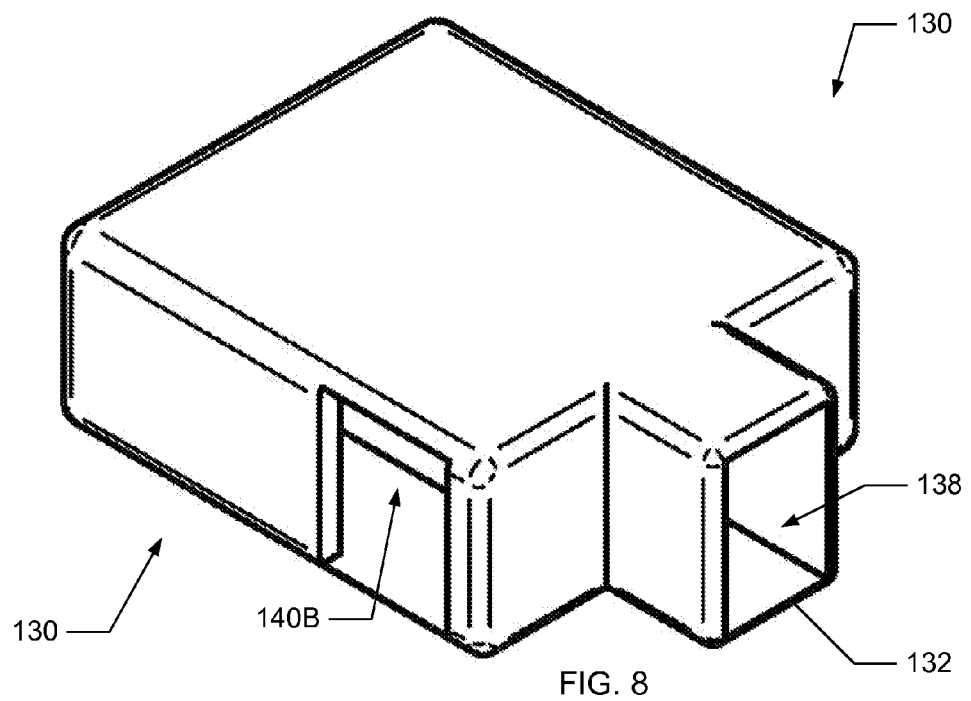
FIG. 8 is a perspective view of a second end of the spirometer mouthpiece according to one embodiment.
Figure 9:
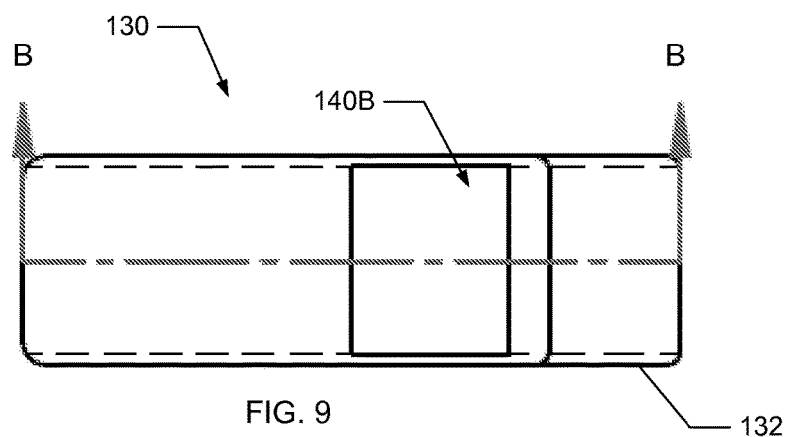
FIG. 9 is a side plan view of an embodiment of the spirometer mouthpiece according to one embodiment.
Figure 10:
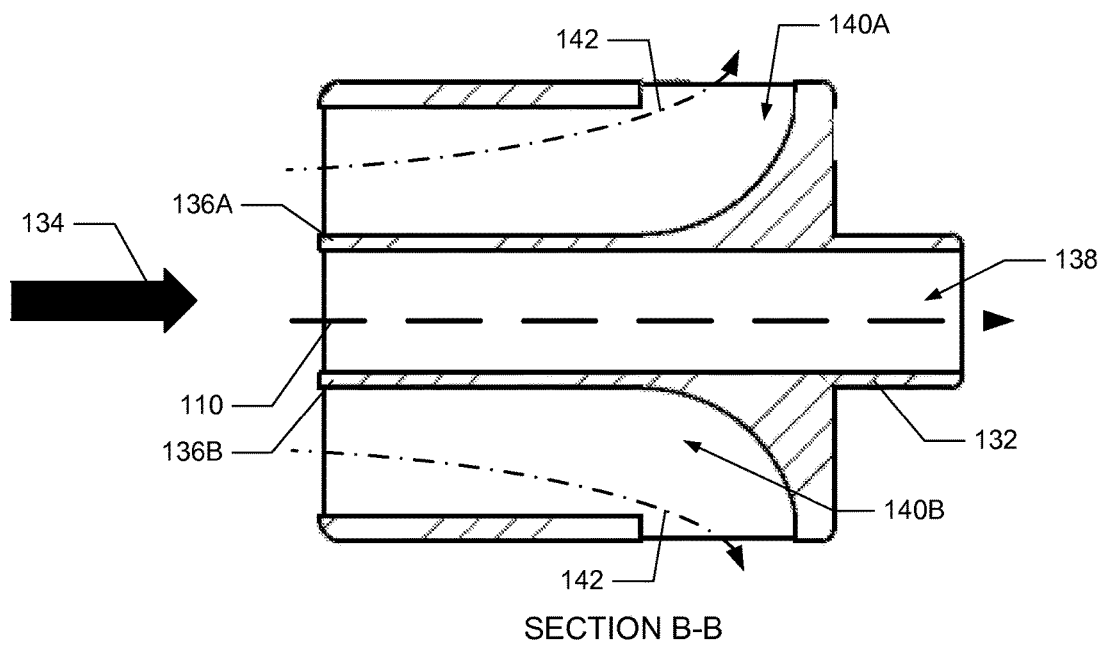
FIG. 10 is a cross-sectional view of the spirometer mouthpiece of FIG. 9, taken along line B-B, according to one embodiment.
Figure 11:
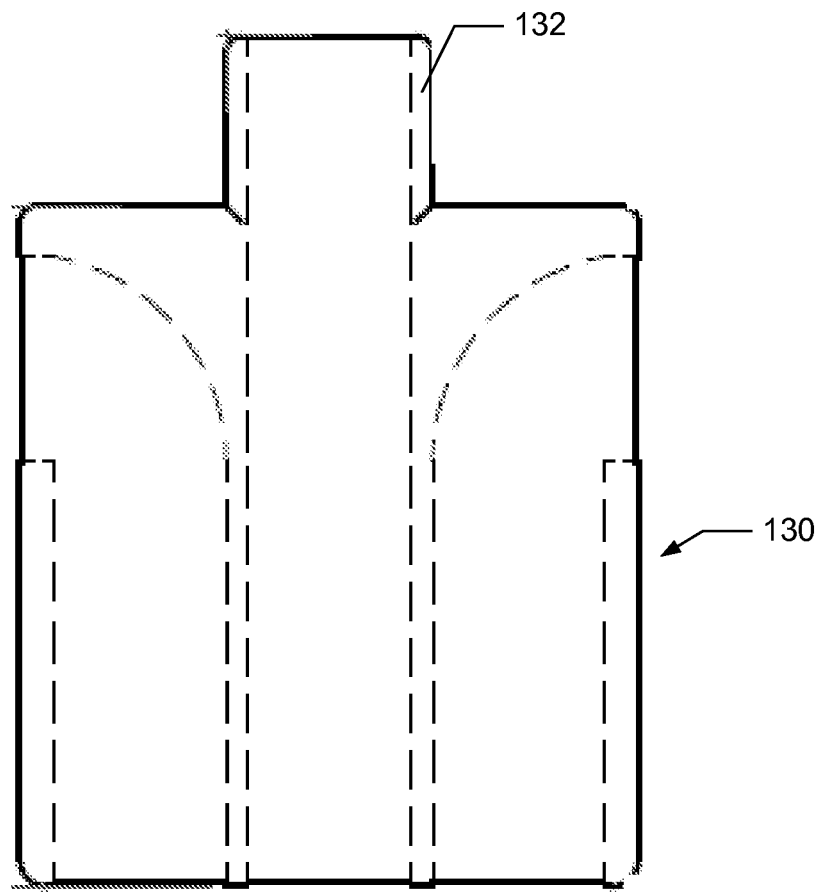
FIG. 11 is a top plan view of the spirometer mouthpiece according to one embodiment.
Figure 12:
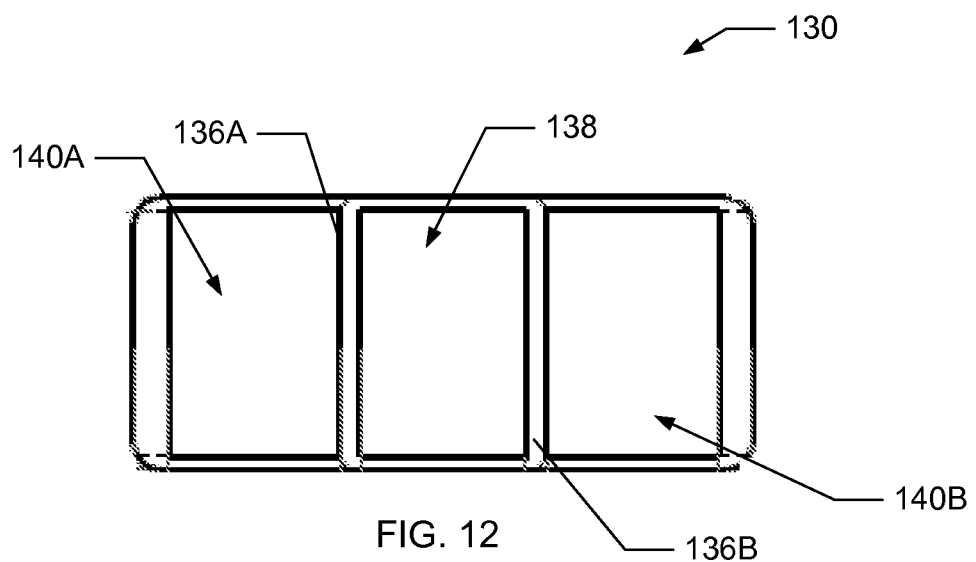
FIG. 12 is a plan view of the first end of the spirometer mouthpiece according to one embodiment.

The present disclosure generally relates to a low-cost spirometer device and software system executing on a computing device to perform analysis of a user's respiratory function. The software system may perform analysis on a data signal generated at the spirometer and provide guidance and feedback to the user.

In various embodiments, a user of the spirometer may exhale and/or inhale through the device. Each exhalation or inhalation through the device may be referred to as a spirometric maneuver. In one aspect, each spirometric maneuver will have characteristics that are detected by a sensor of the device. The data signal generated by the sensor may then be transmitted to a computing device for signal processing and analysis. In various embodiments, the data signal may contain information pertaining to one or more spirometric maneuvers.

FIGS. 1 and 2 are perspective views of one embodiment of the spirometer 100. As shown, this embodiment of the spirometer 100 includes a fluidic oscillator 102 that is at least partially defined by a housing 104, a mouthpiece 130 and a sensor 150. Although described and shown as being integrated with the housing 104, in other embodiments, the fluidic oscillator 102 may be contained within a separate housing or environment.

In one aspect, the fluidic oscillator 102 is defined, at least in part, by the housing 104 to provide two or more pathways or side channels 106A-B for air traveling through the oscillator. The pathways 106A-B are separated by an obstacle 108. In one embodiment, as shown in FIGS. 4 and 5, the obstacle 108 is generally heart-shaped. In this embodiment, an airstream or airflow, indicated generally as 110, entering the fluidic oscillator 102 will first contact a concave surface 112 of the obstacle 108. After contacting the concave surface 112, the airflow 110 is bent or diverted around convex surfaces 114A-B and into one of the two pathways 106A-B, for example pathway 106A as shown in FIG. 4, thereby creating a pressure node at the opposing pathway (e.g., pathway 106B). Collectively, the pathways 106A-B and the obstacle 108 define an oscillation chamber 111 within the housing 104.

In this aspect, the pressure differential caused by the pressure node in pathway 106B causes the airflow 110 to then bend or divert the airflow away from the pathway that it is currently flowing through and towards the pathway containing the pressure node (i.e., pathway 106B). This pattern of the airflow 110 traversing one pathway while generating a pressure node in the opposing pathway, until the pressure differential causes the airflow to switch pathways, occurs continuously while the airflow is entering the fluidic oscillator 102. The frequency with which the airflow 110 alternates or oscillated between pathways 106A-B has a linear relationship to the flow rate of air in the spirometer 102.

As shown, the pathways 106A-B merge into a single outlet 116. The outlet 116 may have any cross-sectional configuration. The outlet 116 is defined by the housing 104. In particular, the outlet 116 is defined by sidewalls 118A-B along with a top wall 118C and a bottom wall 118D.

In one embodiment, at least the distal portions 120 of the sidewalls 118A-B of the outlet chamber are angled linearly outward away from a central longitudinal axis 122 of the spirometer, thereby defining a greater volume for the airflow 110 to flow out of the fluidic oscillation chamber 111, thereby reducing the airway resistance within the chamber.

The spirometer 100 also includes a mouthpiece 130 engaged to the housing 104 for directing the airflow 110 to the oscillation chamber 111 of the fluidic oscillator 102. In one aspect, the mouthpiece 130 is configured to engage an inlet 124 of the fluidic oscillator 102 that is defined by the housing 104. The mouthpiece 130 may be integrated with the spirometer, such that the spirometer may have a solid unitary construction.

In various embodiments, the mouthpiece 130 is detachable from the fluidic oscillator 102. The mouthpiece 130 may be engaged to the fluidic oscillator 102 by a snap-fit engagement, a friction-fit engagement, or any other attachment mechanism. In one particular example, the mouthpiece is threaded and engaged to a corresponding threaded portion of the fluidic oscillator 102. In another embodiment, the mouthpiece 130 is engaged to the oscillator 102 by aligning a projection on the mouthpiece 130 with a corresponding channel on the fluidic oscillator 102. After alignment and insertion, the mouthpiece 130 may be rotated to securely attach the mouthpiece to the oscillator 102.

In one aspect, the mouthpiece 130 may be any solid conduit, including existing spirometer mouthpieces and filters, having a diameter greater than the diameter of the inlet 124 to reduce back pressure within the inlet and the oscillation chamber 111. In this embodiment, the mouthpiece 130 may be a hollow cylinder having a uniform radius along its longitudinal length. In another embodiment, the mouthpiece 130 includes a nozzle 132, as shown in FIGS. 7-11 that is dimensioned to fit within the inlet 124 to form an airtight engagement. As seen in FIG. 4, the nozzle 132 directs a portion of the total airflow 134 generated by a user of the spirometer into the fluidic oscillator.

In this embodiment, the mouthpiece 130 includes one or more baffles 136A-B, to divert a portion of the total airflow 134 such that less than the total airflow in the mouthpiece enters the fluidic oscillator. For example, the airflow 110 that enters the fluidic oscillator 102 may be approximately 50% or less of the total airflow 134. In another example, the airflow 110 that enters the fluidic oscillator 102 may be approximately 30% or less of the total airflow 134.

The baffles 136A-B further define an inlet channel 138 and at least one vent channel. In the embodiment shown in FIGS. 2, 4, 5, and 7-12, the mouthpiece 130 includes two vent channels 140A-B. In other embodiments, the mouthpiece may contain a single vent channel or alternately, may contain three or more vent channels. As shown, the vent channels divert portions of the total airflow 134 away from the fluidic oscillator and vents them to the environment, as indicated by 142.

Figure 13:
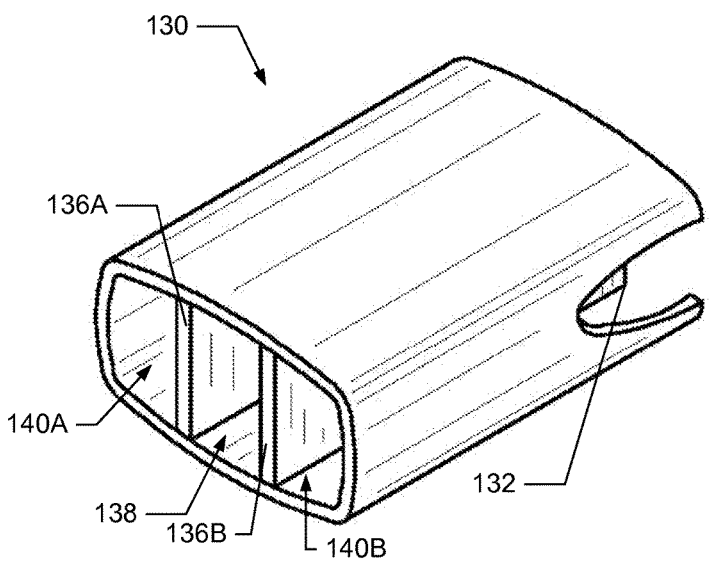
FIG. 13 is a perspective view of a spirometer mouthpiece according to one embodiment.
Figure 14:
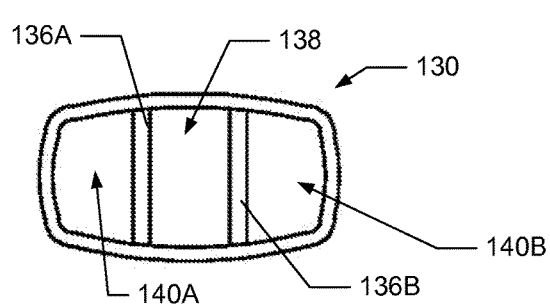
FIG. 14 is an end view of the spirometer mouthpiece of FIG. 13 according to one embodiment.
Figure 15:
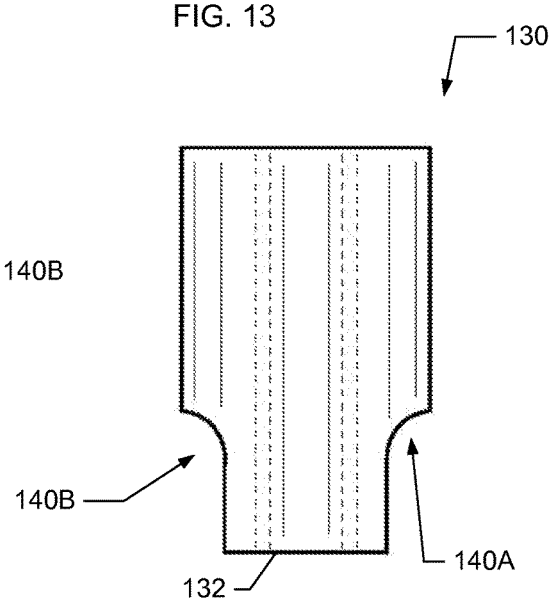
FIG. 15 is a top plan view of the spirometer mouthpiece of FIG. 13 according to one embodiment.

In one embodiment, the vent channels 140A-B may have generally circular cross-sections while the inlet channel 138 has a generally rectangular cross section. In another embodiment as shown, in FIGS. 2, 7, 8, 10, and 12, the inlet channel 138 and the vent channels 140A-B may all have generally rectangular cross-sections. In all embodiments, the mouthpiece 130 is configured to decrease backpressure within the spirometer 100 such that the spirometer operates within guidelines established by the American Thoracic Society Standardization of Spirometry. FIGS. 13-15 depict other embodiments of the mouthpiece 130. As shown in FIGS. 13 and 14, the vent channels 140A-B may have generally hemispherical cross-sections while the inlet channel 138 has a generally rectangular cross section. In various embodiments, the inlet channel 138 and the vent channels 140A-B have cross-sections symmetrically normal to the direction of the total airflow 134. In addition, the baffles 136 A-B and channels 138, 140A, and 140B can generate laminar flow for the turbulent airflow 134 that enters the spirometer.

FIGS. 16-17 depict other embodiments of the spirometer 100 having an integrated inlet 131 thereby forming a single unitary construct. In these embodiments, some of the structure and features of the mouthpiece 130 may be integrated into the housing 102. As such, the inlet includes baffles and channels similar to those previously described.

The sensor 150 may be any sensor suitable for detecting the oscillations of the airflow 110 within the oscillation chamber 111 and generating an electronic signal related to detected oscillations. In various embodiments, the sensor may be a pressure transducer, a piezoelectric sensor, an acoustic sensor, or a thermal sensor, among others. In various embodiments, the sensor is placed along or near an axis of symmetry for the concave surface 112. When the pressure node in the oscillation chamber exerts a large enough force on the jet of airflow 110 in one of the pathways 106A-B and causes it to bend to the other side, the airflow 110 crosses the path of the sensor. In one embodiment, two measured passes of the airflow 110 across the sensor represents one period.

In one embodiment, as shown in FIGS. 3, 21, and 22, the sensor 150 is an acoustic sensor, including but not limited to a microphone. The microphone is positioned proximate to the concave surface 112 of the obstacle 108 to detect and capture the acoustic signal or sound generated by the oscillations of the airflow 110 within the oscillation chamber 111. As described further below, the signal generated by the microphone in response to the captured oscillations may be transmitted to or otherwise received at a computing device, including but not limited to a mobile computing device such as a smartphone, for example.

In one aspect, the sensor 150 may be placed outside of the oscillation chamber. For example, the sensor 150 may be positioned over an opening 152 in the housing 104 that is proximate to the obstacle 108. In another example, the opening 152 may be directly above an area proximate to the concave surface 112. In this example, the sensor is engaged to the housing 104 in an air-tight engagement, such that the airflow 110 does not escape though the opening 152. In yet another aspect, the sensor 150 may be inserted into airflow 110 through the opening 152. In another example, the sensor may be placed flush with the concave surface 112 so that the airflow is normal to the sensor 150.

In another embodiment, the spirometer 100 may include multiple sensors 150. For example, one or more sensors 150 may be placed within or proximate to each of the pathways 106A-B. The placement of at least one sensor 150 in the pathways may further increase the accuracy of the data obtained by the sensor(s). In another example, a sensor 150 may be placed along the axis of symmetry for the concave obstacle surface 112 while another sensor is positioned within one of the pathways 106A or 106B. In this example, the ratio between the frequencies detected by the sensor near the obstacle 108 and the sensor in the pathway would be 2:1. As such sensor along the axis of symmetry would measure two passes of the airflow as a single period, while the sensor along the side channel or pathway would measure one pass as a single period. The combined recorded signals from both sensors would therefore continuously capture both the first and second harmonics of the data signal. In one aspect, the data signals generated by the multiple sensors may provide for greater accuracy during signal processing. For example, a comparison may be made between the two separate frequency curves that are traced out over time as the user exhales. The multiple sensors ultimately yield multiple curves for a single spirometry test. The multiple curves are evaluated and then compared or averaged together, in one embodiment, to create a more accurate result.

As shown in FIGS. 19-21, the sensor 150 may be detachable from the housing of the spirometer 100. In one aspect, the sensor may be housed in a modular sensor housing 154 that is configured to engage the housing 104 of the fluidic oscillator 102. The modular sensor allows for a variety of sensors to be used with the spirometer. For example, the spirometer 100 may include a plurality of sensors 150 that each have their own modular sensor housing 154 and may be interchangeable to capture different characteristics of the airflow 110. In various embodiments, the modular sensor housing may contain multiple sensors, for embodiments of the spirometer that include two or more sensors. Similarly, multiple modular sensor housings, each containing one or more sensor 105, may be used with each spirometer device. FIGS. 18A-C are top views of other embodiments of the spirometer 100. As shown the modular sensor housing 154 may have various shapes and configurations.

The use of a detachable sensor(s) 150 also permits the user to clean or replace the sensor, if necessary. In various embodiments, the sensors and/or the modular sensor housing 154 include one or more membranes positioned over the sensor to protect it from wear and contaminants during exhalation or normal use. In one aspect, the membrane is configured to reduce undesired noise in the recorded signal.

The sensor 150 is configured to transmit an electronic data signal to a computing device. For example, an acoustic sensor, such as a microphone, may include a wire or cable 156 that may be engaged to a computing device to permit communication between the sensor and the computing device. In one aspect, the cable 156 may be received in an audio jack, a USB port, a mini USB port, a micro USB port, or other ports of the computing device, including any proprietary connectors, such as those for Apple® devices. In another example, the sensor may transmit an electromagnetic wave data signal wirelessly to the computing device.

In another embodiment, the computing device may further transmit the data signal to another device over a communication network 408, including the Internet, cellular networks, and/or wireless networks, among others. For example, when a user exhales into the spirometer, an acoustic sensor 150 records the sounds produced by the oscillations. The sensor is also in communication with the computing device via the cable 156. The computing device may store the data locally or further transmit the data via a cellular phone network or other communications network 408, including but not limited to the Internet or other wireless and wired networks to a remote server or website for data analysis. In one example, the remote server or website may be accessible by the patient's healthcare provider, including but to limited to physicians, nurses, and other medical personnel, as well as insurance providers and carriers. The data may also be stored at the remote location and the analysis of the data may be transmitted or sent back to the computing device upon user access to the device or access via the cellular phone network or the communication network.

FIGS. 23-25 depict embodiments of bi-directional spirometers 200 and 300. The bi-directional spirometers 200 and 300 are similar to the spirometer 100 and may use the same mouthpiece 130 and sensor(s) 150; however, the bidirectional spirometers have one or more oscillation chambers 111 such that data can be recorded for airflow 110 traveling both away from (exhalation) and towards (inhalation) the user. The analysis of data for both exhalation and inhalation allows the spirometers 200 and 300 to acquire more quantitative values that characterize lung function.

In one embodiment, shown in FIG. 23, the spirometer 200 has a bi-directional fluidic oscillator 202 defined, at least in part, by a housing 204 to provide two or more pathways 206A-B for air traveling through the oscillator. The pathways 206A-B are separated by a single obstacle 208. In one embodiment, as shown in FIGS. 4 and 5, the obstacle 208 has a generally hourglass or bowtie shape. In this embodiment, airflow, indicated generally as 210, entering the fluidic oscillator 202 will first contact a first concave surface 212A of the obstacle 208. After contacting the first concave surface 212A, the airflow 210 is bent or diverted around a first pair of convex surfaces 214A-B and into one of the two pathways 206A-B, for example pathway 206A, thereby creating a pressure node at the opposing other pathway (e.g., pathway 206B). Collectively, the pathways 206A-B and the obstacle 208 define two oscillation chambers 211A-B arranged in series within the housing 204.

In this aspect, the pressure differential caused by the pressure node in pathway 206B causes the airflow 210 to then bend or divert the airflow from the pathway that it is currently flowing through towards the pathway containing the pressure node (i.e., pathway 206B). This pattern of the airflow 210 traversing one pathway while generated a pressure node in the opposing pathway, until the pressure differential causes the airflow to switch pathways occurs continuously, while the airflow is entering the fluidic oscillator 202. The frequency with which the airflow 210 alternates or oscillates between pathways 206A-B has a linear relationship to the flow rate of air in the spirometer 202.

In one aspect, a portion of the airflow 210 that enters each pathway 206A-B bends around a second set of convex surfaces 214C-D and contacts a second concave surface 212B, where a second set of oscillations similar to those occurring at the first concave surface 212A.

In this embodiment, the pathways 206A-B merge into a single outlet 216. The outlet 216 may have any cross-sectional configuration. The outlet 216 is defined by the housing 204. In particular, the outlet 216 is defined by sidewalls 218A-B along with a top wall (not shown) and a bottom wall 218C.

In one embodiment, at least the distal portions 220 of the sidewalls 218A-B of the outlet chamber are angled linearly outward away from a central longitudinal axis 222 of the spirometer, thereby defining a greater volume for the airflow 210 to flow out of the fluidic oscillation chamber 211, thereby reducing the airway resistance within the chamber.

The bi-directional spirometer 200 includes one or more sensors, similar to the sensor 150 that may be positioned proximate to concave surfaces 212A-B, as indicated by 230A-B. Each sensor 150 may be placed external to the oscillation chamber 211 or may be inserted into the airstream or airflow 210 at positions 230A-B. In other embodiments, additional sensors may also be used to gather data from the airflow in one or more of the pathways 206A-B. In yet another embodiment, the one or more sensors 150 may configured to record data from multiple inputs. For example, a microphone sensor may be configured to records acoustic signals at multiple locations simultaneously, similar to the multi-channel signals used in audio/visual equipment.

Each oscillator chamber 211A-B may be associated with a single shared sensor 150 or alternately, each may be associated with their own sensor 150. The sensors for each oscillator chamber 211A-B may be the same type of sensor, including but not limited to acoustic sensors, thermal sensors, and pressure transducers, among others. Conversely, each oscillator chamber 211A-B may use different types of sensors to collect data.

The bi-directional spirometer 300 has shown in FIGS. 24-25, includes two or more unidirectional fluidic oscillators 302A-B, similar to the fluidic oscillator 102 that is arranged in parallel. In particular, the fluidic oscillators 302A-B are arranged in a stacked configuration, where the fluidic oscillator 302A is configured for oscillation during exhalation (air flowing in a forward direction) and lies on top of the fluidic oscillator 302B that is configured for oscillation during inhalation (air flowing in a reverse direction). For example, a user may exhale through the spirometer 300 to generate airflow oscillations in the first fluidic oscillator 302A, and inhale to generate oscillations in the second fluidic oscillator 302B. In this embodiment, the outlet 316 for the spirometer 300 functions as an inlet during inhalation.

In various other embodiments, the spirometer may include multiple bi-directional spirometers, such as the bi-directional spirometer 200, in a stacked arrangement similar to the bi-directional spirometer 300. Other arrangements, configurations, and sizes of unidirectional and bidirectional spirometers may be used.

In this embodiment, each oscillator 302A-B may be associated with a shared sensor 150 or alternately each may be associated with their own sensor 150. The sensors for each fluidic oscillator 302A-B may be the same type of sensor, including but not limited to acoustic sensors, thermal sensors, and pressure transducers, among others. Conversely, the spirometer 300 may include different types of sensors for each fluidic oscillator 302A-B. Similar to the other embodiments of the spirometer 100 and 200, the spirometer 300 may include additional sensors, positioned in one or more of the pathways 316A-D for the fluidic oscillators 302A-B.

Figure 26:
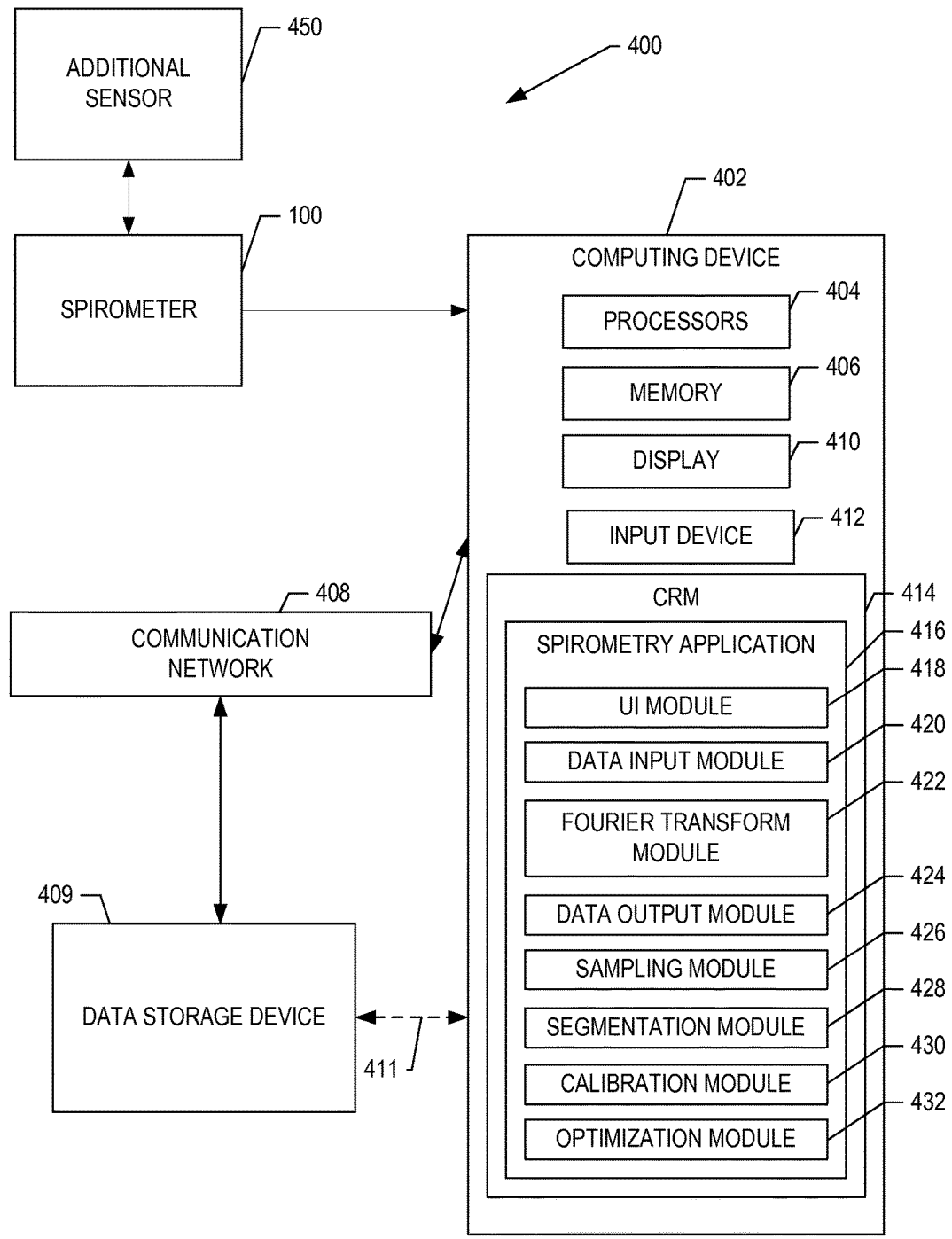
FIG. 26 is a block diagram of a system and computing environment for collecting and analyzing spirometric data according to one embodiment.

FIG. 26 is a block diagram of one embodiment of a system 400 and computing environment for collecting and analyzing spirometric data using a spirometer 100 and computing device 402 executing a spirometry application 416. In various aspects, data collected using the spirometer 100 is transmitted to the computing device where the spirometry application is used to perform signal processing and data analysis. Although the system 400 is shown and described as using the spirometer 100, the other embodiments of the spirometer 200-300 may also be used.

In various embodiments, the spirometer 100 may include one or more additional sensors or monitors, indicated as 450 to gather additional data. These additional sensors 450 may be integrated with the spirometer 100 or may be in communication with the spirometer 100 or computing device 402. For example, the additional sensor 450 may be an external air-monitoring device that measures air quality, allergens, temperature, and/or other environmental data. In another example, an additional sensor 450 is an inhaler monitoring device. For example, the spirometer 100 can communicate with a device that tracks medication usage (e.g., the GeckoCap or the Asthmapolis system), which are electronic devices engaged to an inhaler that record each time the inhaler is used and the location of usage.

In yet another example, the additional sensor 450 may be an activity sensor. In this example, the spirometer 100 communicates with activity based sensors, such as but not limited to sensors that collect data from shoes, a watch or wristband, such as the Nike Fuelband™, a FitBit™, Misfit™, Basis™ or other sensors. In this example, the spirometer system 400 can be used to better understand how factors, such as activity level and heart rate, among others, affect or are affected by respiratory function. In another example, the additional sensor 450 may also be a pulse oximeter.

The computing device 402 includes one or more processors or processing systems 404 and volatile and/or non-volatile memory 406 and is configured to receive data and/or communications from, and/or transmit data and/or communications to other computing devices (not shown) via a communication network 408. Examples of a computing device 402 include smartphones, tablet computers, desktop computers, servers, and other computing devices. The computing device 402 communicates via wireless and/or wireline communication.

The computing device 402 communicates with and stores data on a data storage device 409. In one embodiment, the data storage device is a remote external storage device, such that the computing device 402 may retrieve and store data via the communication network 408 in a cloud computing environment. In another embodiment, the data storage device 409 may be incorporated with the computing device 402 or at least communicate directly with the computing device, as indicated by 411.

The computing device 402 also includes a display 410, such as a computer monitor or screen, for displaying data and/or graphical user interfaces. The computing device 402 may also include an input device 412, such as a keyboard or a pointing device (e.g., a mouse, trackball, pen, or touch screen) to enter data into or interact with graphical user interfaces. The computing device 402 also includes a computer readable medium ("CRM") 414 configured with a spirometry application 416.

According to one aspect, the CRM 414 may include volatile media, nonvolatile media, removable media, non-removable media, and/or another available medium that can be accessed by the computing device 400. By way of example and not limitation, the CRM 414 comprises computer storage media and communication media. Computer storage media includes nontransient memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

The spirometry application 416 includes instructions or modules that are executable by the processing system 404 to receive and analyze data collected from the spirometer 100 that relates to various characteristics of the airflow 110 within the fluidic oscillator 102 and provides information and guidance to the user. For example, the application 416 may use data collected from each spirometric maneuver in the fluidic oscillator (spirometric data) and environmental data relevant to the user's location to warn the user of potential adverse environmental conditions that may affect the user's respiratory function. As described more fully below, the spirometry application 416 may perform a Fourier transform on the data signal to produce a spectrum relative to the spirometric maneuver(s). In addition, for each spectrum, the frequency of maximum intensity may be located and recorded. Each frequency of maximum intensity may be derived from an average of the specific oscillation frequencies for that set time interval. These frequencies are then converted to flow rates using a process of Linear Flow Rate Calibration. Each newly converted flow rate is then plotted at its corresponding time interval to create Flow Rate vs. Time plot(s). From these plots, spirometric data, including but not limited to forced vital capacity (FVC), volume that has been exhaled at the end of the first second of forced expiration ($FEV_1$), peak expiratory flow (PEF), and many other spirometry values can be calculated by calibrating the data and integrating the plot with respect to time.

In one embodiment, the spirometry application 416 includes a user-interface (UI) module 418, a data input module 420, a Fourier transform module 422, and a data output module 424. In addition, the spirometry application 416 includes a sampling module 426, a segmentation module 428, a calibration module 430, and an optimization module 432.

In other embodiments, the spirometry application 416 may include additional modules. In all embodiments, the functionality of each module may be shared and performed by one or more other modules. In addition, in at least one embodiment, the modules or, at least the functionality of each module, may be distributed across one or more computing devices in communication via the communication network 408.

Figure 32:
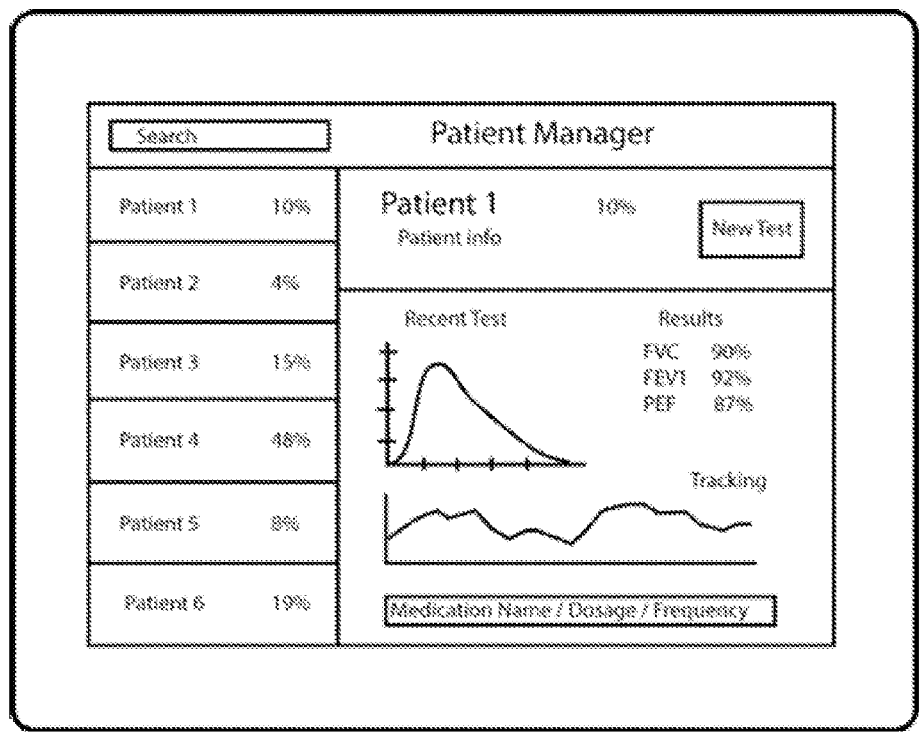
FIG. 32 depicts a user interface generated on a tablet by the spirometry application according to one embodiment.
Figure 33:
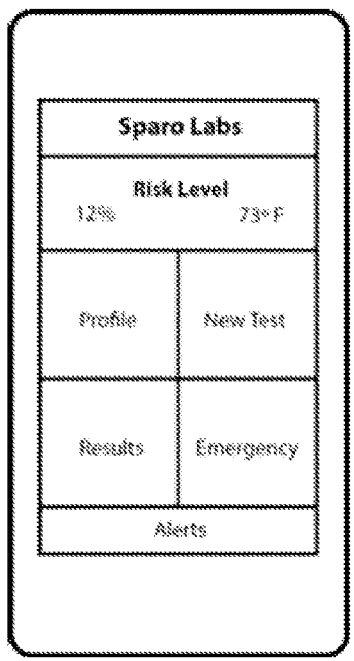
FIGS. 33-34 depict user interfaces generated on smartphones by the spirometry application according to one embodiment.
Figure 34:
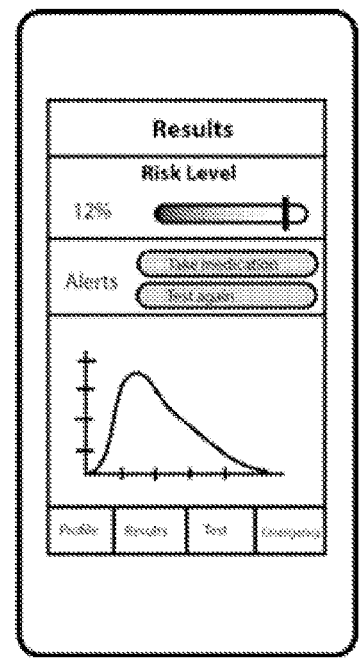

The UI module 418 generates one or more user interfaces, including input forms for display at display 412. For example, a user of the spirometry system 400 uses the input device 412 to interact with, for example, the spirometry application 416 or a web browser, via a user interface to access, interact and display data or other interfaces generated by the spirometry application. Example user interfaces 1000A-C are depicted in FIGS. 32-34.

The data input module 420 receives data from the spirometer and the user. The data received includes spirometry data, such as but not limited to the data signal, including audio signals that relates to an airflow vs. time curve, all relevant spirometry values, such as FVC, $FEV_1$, and PEF.

The data input module 420 also receives metadata for each spirometry test, user symptoms, medication usage, or other input data. In one aspect, the metadata includes geo-location data, such as the date, time, and location of the user during the spirometer test. The location may be obtained from GPS data of the computing device or derived from the communications network of the computing device. The metadata also includes environmental data, including but not limited to the temperature, barometric pressure, humidity, air quality index, local allergen and pollutant data (e.g. pollen counts, mold counts, etc.).

Fourier transform module 422 performs Fourier transforms on the data signal. This module may perform any Fourier transform or wavelet transform, including but not limited to a short-time Fourier transform (STFT), to analyze the frequency spectrum at set time intervals.

The data output module 424 generates data that may be displayed in one or more user interfaces or data forms. In one aspect, the data output module provides health assessment or risk assessment level interface to the user. In one aspect, the health or risk level of a user may be determined by comparing results from one or more spirometry tests to predicted test results. In this aspect, deviation from the predicted results may cause a change in the health or risk level assessment. The health or risk level assessment includes aggregated symptom data along with spirometry results, location and environmental data, weather data, and other relevant data. In one embodiment, the health or risk level assessment is provided on a continuous spectrum having a range from 0% to 100%, where a greater percentage is indicative of increase risk. The health assessment also presents the user with actionable items, such as how often to perform a spirometry test that day, as well as when to take a test based at least in part on the user's health or risk assessment level. As the risk level changes based on the timing of the test, in various embodiments, more recent tests or symptom would be weighted more heavily in computing the current health or risk assessment level. The test results would then decrease in value over time, as new data is added.

The data output module 424 also allows users to store data in a cloud network. For example, the user can create a credential-based account to access their data via mobile devices or online via a web application or mobile applications (apps). In one aspect, caregivers and healthcare providers can connect with patient accounts to access patient data and monitor numerous patients. In addition, the data output module is configured to integrate with various electronic medical records systems.

In another aspect, the data output module may generate alerts to caregivers and healthcare providers (via email, mobile application alerts, text message, etc.) when needed. These alerts may be generated, for example, after a symptom or attack, after an abnormal spirometry result, if a patient has not taken medicine in a predetermined number of days or other set time period, or after an elevated or adverse health or risk assessment level is reached (e.g., ≥50% risk of an adverse respiratory event, such as an asthma attack, among others). Other criteria may also be used to generate an alert.

The data output module may also communicate and integrate with a user's asthma action plan, which tells users what actions to take based upon PEF, FEV1, or risk assessment level results. In addition, the data output may forecast future risk levels for future days based upon forecasted environmental data or weather conditions. The output module 424 also generates one or more user interface displays with the results of the forecast as well as the factors that are the most relevant for each day or forecasted time period. The forecast time periods may be in a range between hours and months.

The sampling module 426 samples the data signal and in one embodiment, reduces the sampling rate of a signal by down sampling. The segmentation module 428 divides the data signal into discrete segments to identify portions of each spirometric maneuver such as the starting or initial points and the end points. In addition, the segmentation module 428 may also recombine segments of the data signal at any point during signal processing to further optimize the processed signal.

The calibration module 430 executes one or more calibrations equations and algorithms to calibrate the spirometer device 100 and the data signal received therefrom. Similarly, the optimization module 432 executes one or more equations and algorithms to optimize the functionality and results of the other modules 418-430 and modules 434-444, as described below with reference to FIG. 31.

After a user performs a spirometric maneuver with the spirometer 100, the data gathered by the sensor 150 is transferred for analysis external to the spirometer. In preferred embodiments, the analysis of the data signal occurs external to the fluidic oscillator 102. As such, any circuitry or other electronic elements, including the sensor 150 in some embodiments, are external to the fluidic oscillator, thereby allowing for easy cleaning of the spirometer 100. However, in at least one embodiment, the spirometer may be a standalone device having integrated a microprocessor and memory to record, process, and store the data. This embodiment may also be configured to communicate with an external device.

In various embodiments, the data signal or the data within the data signal may be transmitted via text or media message, via a direct connection to a computing device, via phone call or via the Internet. The information may be analyzed at a local computing device, smartphone, a remote computing device, a web server, a website, or a voicemail service, such as Google voice.

By way of example and not limitation, a data file transferred to a smartphone or cell telephone, may be sent through a cell phone or wireless communication network in the form of a text message to a website that analyzes the data and then sends the analysis back to the user over the cellular or wireless network. In another example, the data file may be sent through cell phone communication in the form of a phone call to a website that stores the message as an audio file. The audio file is then uploaded to a website that analyzes the data and sends the analysis back to the user over the phone.

In yet another example, the data signal may be captured directly by one or more applications, such as the spirometry application 414, previously described with reference to FIGS. 26 and 31, executing on the smartphone, tablet, or cell phone. In this example, the analysis is performed on the smartphone and displayed to the user. In a similar example, the data signal is captured directly at a desktop or laptop computing device that stores the data and analyzes the data via a program or application, such as the spirometer application, executing on the computing device. In addition, the local computing device may transmit the data to a remote computing device, such as a server for analysis.

Figure 27:
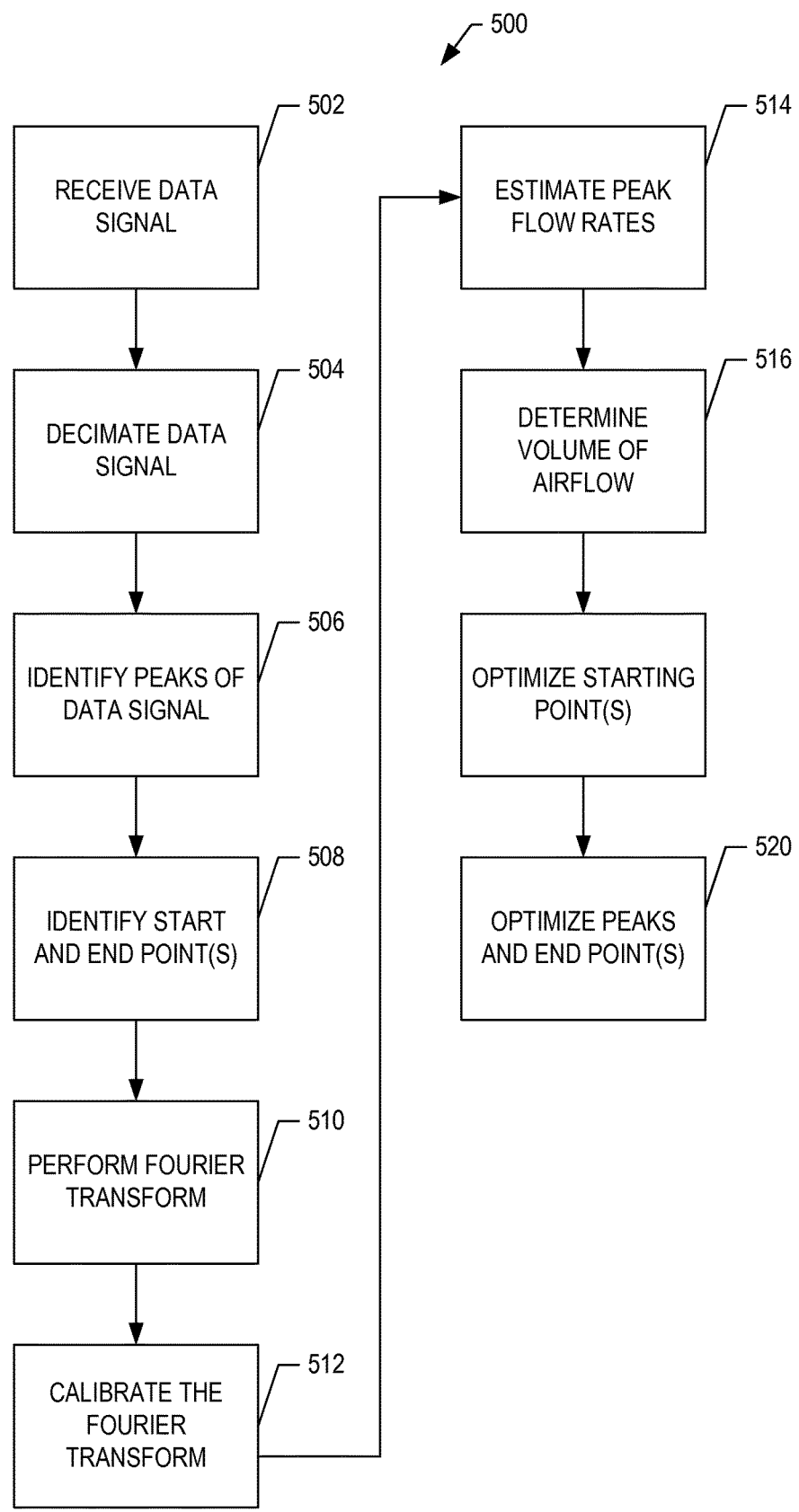
FIG. 27 is a block diagram depicting a signal-processing method for analyzing data from a spirometer device according to one embodiment.
Figure 28:
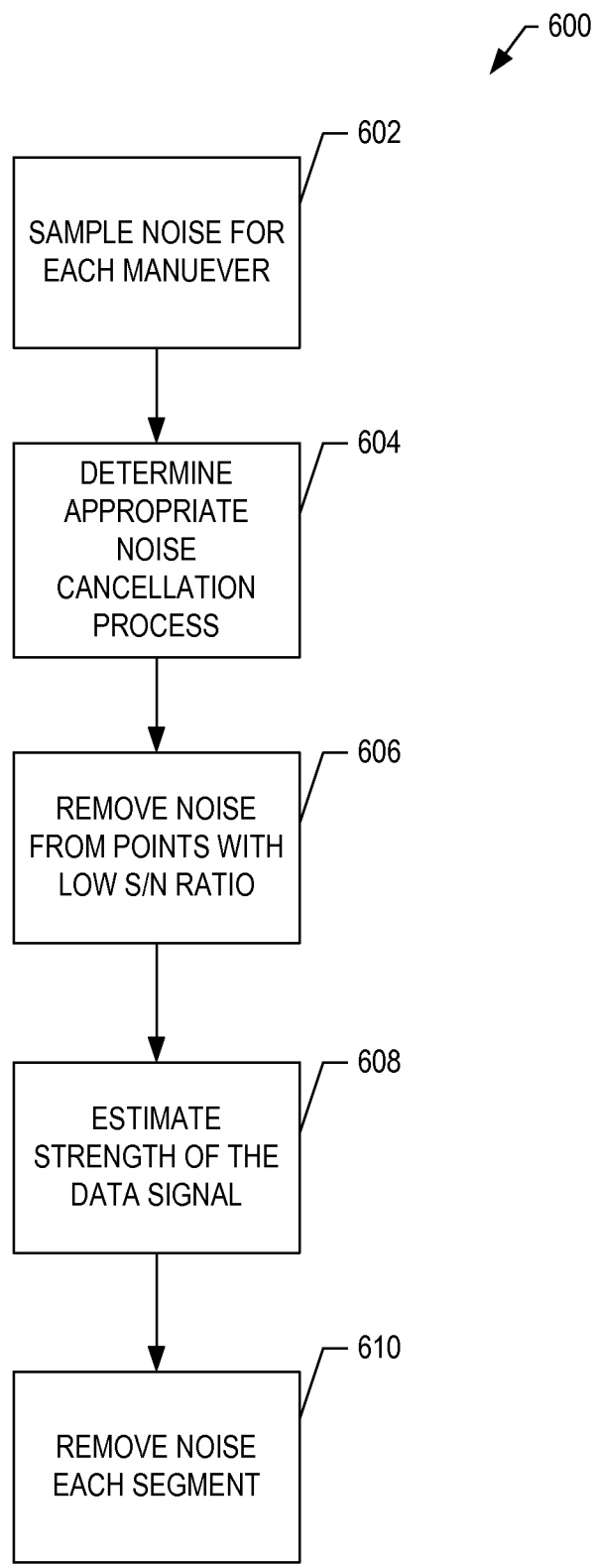
FIG. 28 is a block diagram depicting a signal-processing method for analyzing data from a spirometer device according to one embodiment.
Figure 29:
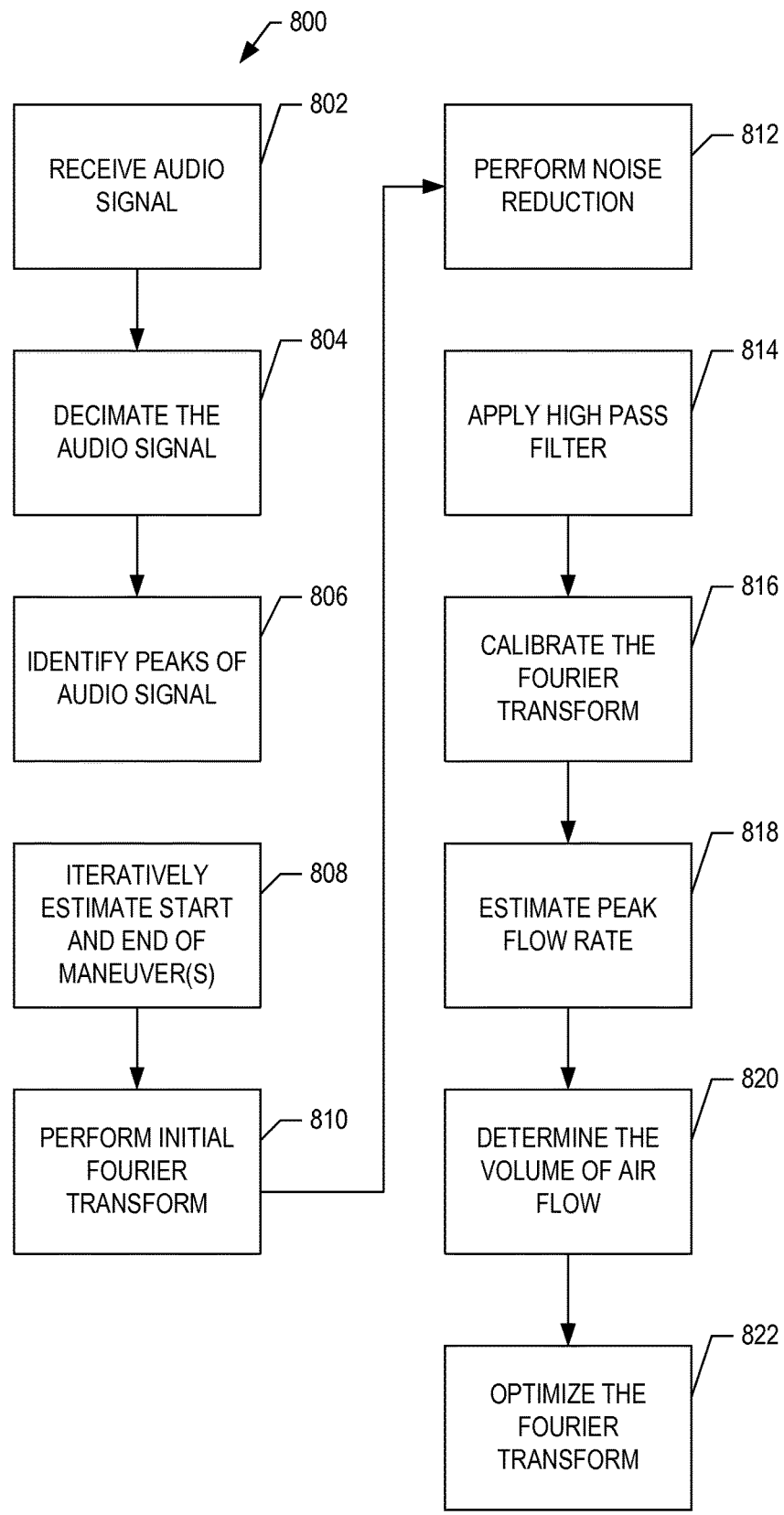
FIG. 29 is a block diagram depicting a signal-processing method for analyzing data from a spirometer device according to one embodiment.

FIGS. 27-29 are block diagrams depicting various methods 500-800 for processing and analyzing the data signal received from the sensor 150 of the spirometer. In one aspect, the method may be performed on the spirometric data using the spirometry application 416.

In one embodiment, after a user of the spirometer 100 exhales or inhales through the device and the sensor 150 records the sound generated by the oscillation of air passing through the device, a data signal, which may be an audio signal in one embodiment, containing data related to the oscillations of air is received at the computing device 402, at block 502. At block 504, the audio signal is down sampled or decimated at the sampling module 426 of the spirometry application 41. In one aspect, the decimation of the signal prevents aliasing at the Nyquist's frequency. At block 506, the peaks of the data signal are identified through iterative estimation at the segmentation module 428, and at block 508, the segmentation module identifies the starting and ending points for each spirometry maneuver in the signal.

At block 510, the Fourier transform module 422 performs multiple Short-Time Fourier Transforms (STFT) with varying window sizes on the data signal, in one embodiment. In other embodiments, the Fourier transform module 422 may perform a wavelet transform instead of or in addition to the STFT. After transformation, the maximum frequency within the spirometric maneuver is identified. Signal characteristics, such as the derivative of the data signal, the signal to noise ratio, and the signal power or intensity are then determined and used along with the maximum frequency to define a number of threshold or breaking points where the data signal will be segmented by the segmentation module 428. As determined by the characteristics present in each segment, the segments will be drawn using the optimal STFT to increase accuracy of the data. For example, as the window size of the STFT changes the temporal or frequency resolution, it is desirable to identify the best window size(s) to optimize both the temporal and frequency resolution for each specific section of the frequency vs. time curve. The optimal STFT window size is determined by the slope of the curve (i.e. the frequency range present in a section divided by the change in time in a section). Therefore, it is ultimately the slope of the curve that determines the most appropriate STFT window size.

At block 512, a calibration equation relating the frequency to the flow rate for the optimized STFT is executed at the calibration module 430. The optimization module 432 determines the volume of the airflow 110 by integrating the flow rates at block 516.

In various embodiments, the spirometry application 416 is also configured to reduce the noise within the data signal. For example, the spirometry application 416 may be used to perform a method 600 for reducing both the static noise and the dynamic noise within the data signal, as shown in FIG. 28. At block 602, the spirometry application 416 employs adaptive noise cancellation after an initial analysis of the specific characteristics of the data signal. Based on those characteristics, the application 416 chooses the most appropriate methods of noise cancellation to use on the signal. For example, this may be based on the amount of static or dynamic noise present in each segment of the data signal. In addition, noise present in the signal could also be evaluated or quantified based on the measured or extrapolated flow characteristics (e.g., laminar or turbulent flow) of the air passing through the spirometer device.

For example, to reduce static noise, the sampling module 426 performs differential noise cancellation by sampling the noise between each spirometric maneuver or before and after a single maneuver at block 604. At block 606, the sampling module 426 then removes the noise from portions of the signal for which this type of noise effects the quality of the data, namely where the signal to noise ratio is small (e.g., ≤2:1 (signal:noise)). Similarly, to reduce dynamic noise, the sampling module estimates the strength of the signal at block 608. In one aspect, where the data signal is an audio signal, the data signal received from the sensor 150 is known to be continuous during each spirometric maneuver; therefore, the sampling module estimates the signal value rather than estimating the noise, as done in traditional approaches to noise reduction for audio signals. At block 610, the appropriate noise cancelling process or algorithm for each segment is applied to remove dynamic noise from the data signal.

Similarly, the application 416 may perform an adaptive flow rate determination process. For example, after analyzing specific characteristics of the data signal, the application 416 chooses the most appropriate method(s) to compute flow rates for each part of the signal based on the characteristics of the data signal. For example, the flow rate may be determined using calibration curves including a frequency vs. flow rate curve or an amplitude vs. flow rate curve.

FIG. 29 is a flow diagram of another method 800 for processing and analyzing an audio data signal received from an acoustic sensor 150. The method may be performed using the various modules 418-432 of the spirometry application 416. The audio signal is received at the computing device 402 at block 802. At block 804, the audio signal is decimated to prevent aliasing based on Nyquist's frequency, while at block 806 the peaks of the audio signal are found. The start point and the end point of each spirometry maneuver in the audio signal is identified at block 808 and several STFTs with varying parameters are performed on the full signal at block 810.

Noise reduction is performed on each segment at block 812 by applying a bandpass filter to the STFT of the data signal, as the upper and lower boundary for the frequency range is known. As the data signal is a continuous signal, the boundaries for each segment are identified by breaking points based on the peak flow rate within the data signal. At block 816, a calibration equation relating frequency to flow rate is applied to the STFT of the data signal. The locations of the peak flow rates are determined at block 818 and the flow rate is integrated to determine the volume of air passing through the spirometer at block 820.

At block 822, the STFT is optimized. In one aspect, this includes segmenting or dividing the spirometric maneuver into four sections based on the ratio of each frequency to the maximum frequency within that maneuver. The STFT parameters are then specified for each section of the curve based on the frequencies present in each specific section to increase accuracy. Noise reduction is applied to each STFT section depending on the characteristics of that section. For example, the need for noise reduction is determined by the noise present, the signal-to-noise ratio, and the sections location in the maneuver cycle. The noise reduction may be performed using various techniques, including but not limited to the use of high pass filters and low pass filters, differential noise cancellation, using moving averages and any other filtering techniques. An optimized and continuous STFT is produced by piecing together the sections and their related STFT based on the intervals determined from the segmentation of the curve.

Figure 30:
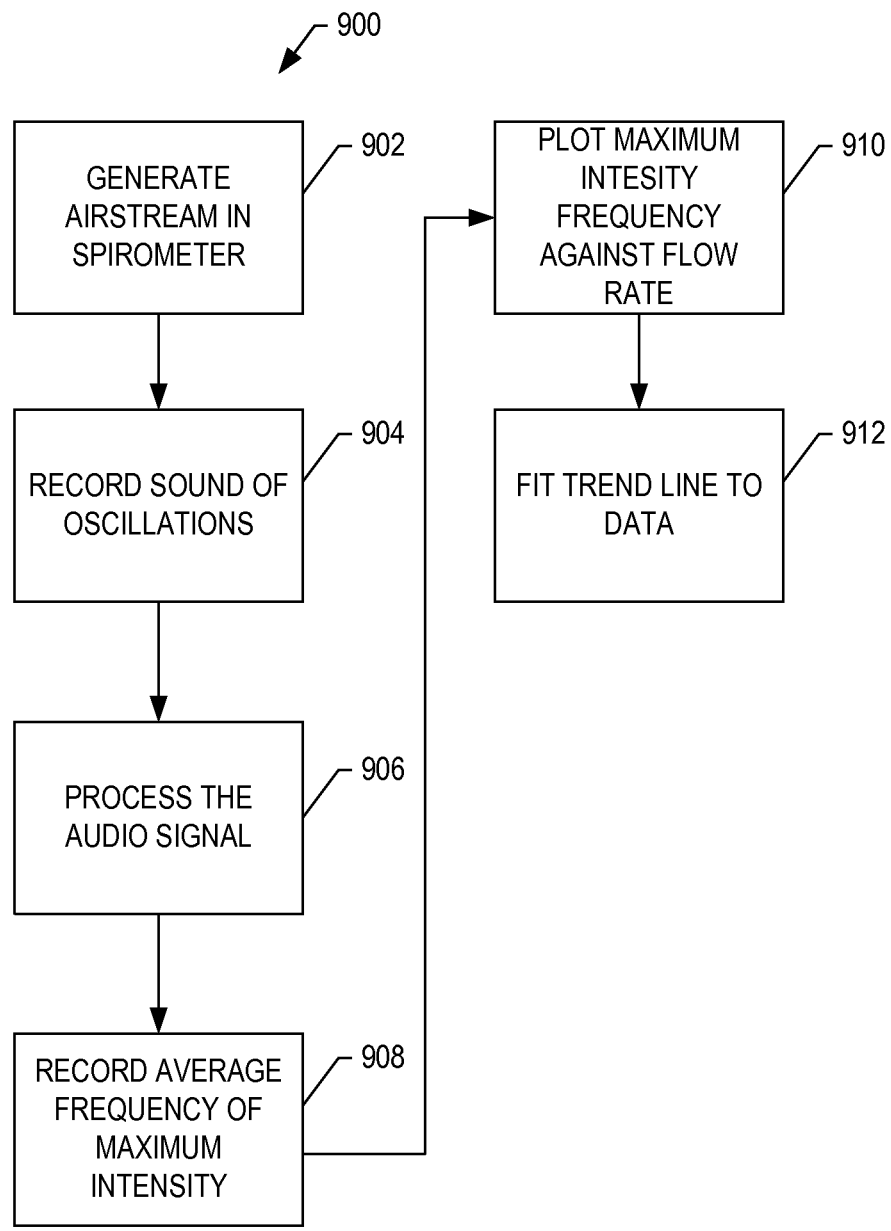
FIG. 30 is a block diagram depicting a method for calibrating a spirometer device according to one embodiment.

FIG. 30 depicts a method 900 for calibrating the linear flow rate of the spirometer 100, 200, or 300, to determine the relationship between the oscillation frequency and the flow rate. At block 902, an airstream is generated by a compressor, passed through a regulator and a variable area flow meter, and finally through the spirometer. In one aspect, the regulator is used to set a specific flow rate, which is then recorded using the flow meter. At block 904, the sensor 150 on the spirometer records the sound of the oscillations, and the recorded data file undergoes the same or similar method, previously described with reference to FIG. 27 at block 906. The average frequency of maximum intensity is recorded at block 908. As the incoming flow rate is known and constant, the frequency of maximum intensity can be directly related to the known flow rate. At block 910, the frequency of maximum intensity is recorded and plotted against the flow rate for various flow rates and a trend line is then fit to the data points at block 912 to establish a linear equation that is largely independent of environmental factors, such as humidity, elevation, and pressure, can determine the flow rate for any given frequency.

Figure 31:
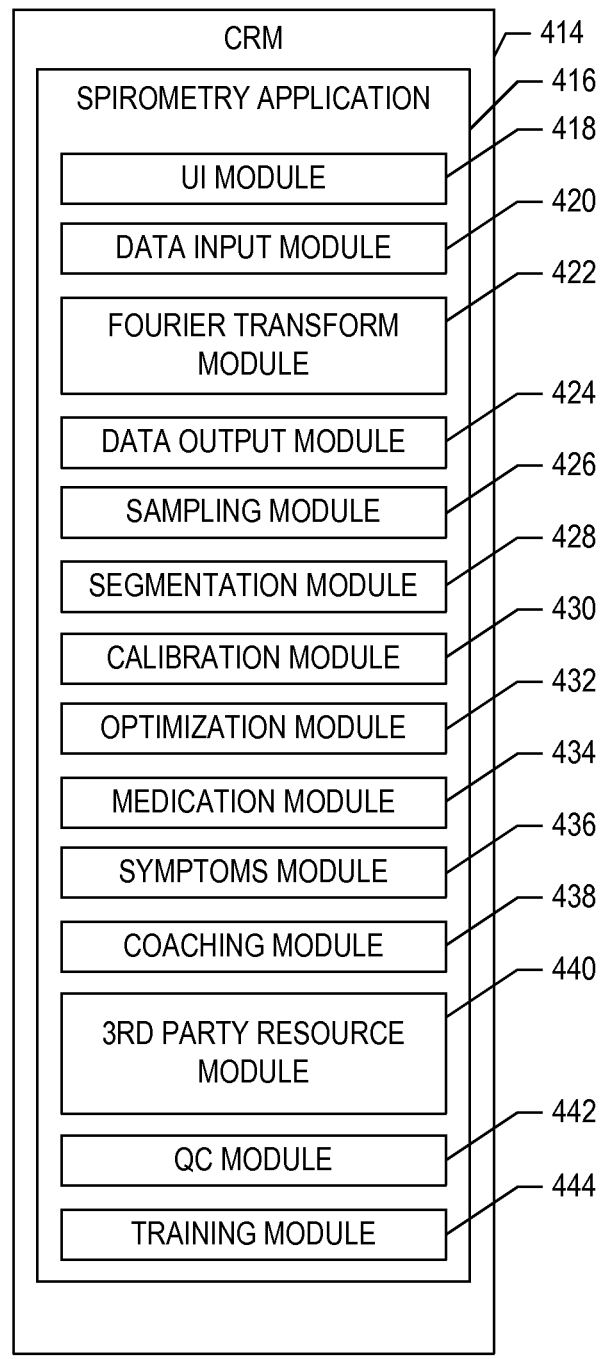
FIG. 31 is an embodiment of a spirometry application, executable on a computing device, according to one embodiment.

As shown in FIG. 31, another embodiment of the spirometer application 416, as encoded on a CRM 414, may include additional modules for performing additional functions in addition to analyzing the spirometric data. The application 416 may also include a medication module 434, a symptoms module 436, a coaching module 438, a third-party resource module 440, a quality control module 442, and a rehabilitation/athletic training module 444.

The medication module 434 allows the user to establish a schedule for taking medications including identifying what medication is to be added, the dosage, frequency, and other relevant information. In one aspect, the medication module 434 alerts patients to take medication through text messages, emails, social media messages, as well as mobile phone alerts/notifications or app alerts/notifications. In addition, the medication module 434 includes "snooze" functionality where a user can postpone or delay their medication alert if they are unable to take their medication at that time. For example, the application 416 can be configured to remind the user again with another alert in a set period of time (e.g. 15 min, 30 min, 60 min, etc.).

The medication module 434 also generates one or more user interfaces to accept input by the user to confirm that the medication was taken. The medication module 434 will then log this event as well as any relevant time/location/environmental data. In another aspect, the medication module 434 can recommend or determine an adjustment for the dosage of the medication within a set range based on symptoms, spirometry results, or other relevant criteria. Additionally, in another aspect, a caregiver or healthcare providers can remotely review or set medication information or alerts for a user at any time.

The symptoms module 436 prompts the user to log any respiratory related symptoms within the application or on external media. For example, the symptoms module 436 may generate a user interface to log symptoms at a variable period before or after a spirometry test. The period may be, for example, every 3 hours, just before or after a spirometry test, or just before or after taking a medication. Other periods may also be used.

The coaching module 438 provides real-time guidance and coaching to the user during the spirometry maneuvers and test. For example, the coaching module 438 uses pre-recorded encouragements or sound/musical encouragements. In a particular example, the coaching module 438 plays an ascending major scale as the user blows through the device, where each note of the scale is reached as the patient gets closer to maximal effort. In another example, the coaching module 438 provides visual encouragement, including the use of games to induce maximal effort from the user. In another aspect, the coaching module 438 provides post-test coaching and informs the user what actions to take after the test. For example, the coaching module 438 may identify shortcomings in the most recent test to prompt a better result the next time through audio and visual reminders or encouragement.

In another aspect, the coaching module 438 also incorporates educational resources to help patients better understand their respiratory condition, for example asthma, and help them understand what they can do to better manage the condition. For example, the coaching module 438 includes an educational resource database where users can learn about their disease including how to take medication, how to do spirometry, and how to identify their disease triggers, among other data.

The third-party resource module 440 allows researchers to interact with and customize the portions of the spirometry application 416 to design and implement studies or protocols. The researchers may push messages or forms to specific users or groups of users and track data from multiple groups to perform analysis by comparing users across and within various groups.

The quality control module 442 identifies the errors in a spirometry test. For example, the quality control module 442 determines whether the test needs to be conducted again and informs the user of what changes are necessary to collect usable data. In one aspect, the module uses an algorithm to compare the test to previous approved tests or set ranges for various spirometric values.

The rehabilitation/athletic training module 444 is useful to athletes or users undergoing rehabilitation to assess athletic performance and/or lung function. In one aspect, the training module 444 detects how the user is breathing to determine if the user is using the full capacity of their lungs when breathing or a specific percentage. In addition, the training module 444 measures the user's breathing recovery time after physical exertion via various spirometry tests. In another aspect, the module includes games or coaching for users during breathing exercises or spirometry tests.

The description above includes example systems, methods, techniques, instruction sequences, and/or computer program products that embody techniques of the present disclosure. However, it is understood that the described disclosure may be practiced without these specific details. In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

Portions of the described disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology.

What is claimed is:

1. A device for measuring a continuous flow rate of an air stream comprising:
    a fluidic oscillator;
    a nozzle to direct a portion of the airstream into the fluidic oscillator;
    a detachable mouthpiece to reduce back pressure within the device, wherein the detachable mouthpiece defines a plurality of channels, at least one of the plurality of channels directs the portion of the airstream to the nozzle and at least one other channel vents another portion of the airstream to an environment external to the device;
    the fluidic oscillator having a housing and at least one obstacle, to induce oscillations in the airstream, wherein a frequency of the oscillations correlates to the continuous flow rate of the airstream; and
    at least one sensor to measure the oscillations of the airstream, the at least one sensor to generate an electronic signal corresponding to the oscillations measured and transmit the electronic signal to a computing device.

2. The device of claim 1, wherein the detachable mouthpiece is removably engaged to the fluidic oscillator.

3. The device of claim 2, wherein the detachable mouthpiece is removably engaged to the fluidic oscillator through at least one of a snap-fit engagement, a friction-fit engagement, a threaded engagement, or a rotated projection engagement.

4. The device of claim 1, wherein the at least one channel and the at least one other channel are configured to divide the portion and the other portion of the airstream in a fixed ratio.

5. The device of claim 4, wherein the portion of the airstream vented to the ambient air is no less than one-half of the airstream.

6. The device of claim 1, wherein the portion of the airstream vented to the environment is at least two-thirds of a total volume of the airstream.

7. The device of claim 1, wherein the at least one channel and the at least one other channel each has a cross-section symmetrical normal to the direction of the airstream.

8. The device of claim 1, wherein the at least one channel and the at least one other channel correlate to at least one of the area of the incoming airstream, an average flow rate of the airstream, a maximum flow rate or a specific flow rate of the incoming air stream.

9. The device of claim 1, wherein the at least one channel and the at least one other channel convert a turbulent flow of the airstream to a laminar flow before entering the fluidic oscillator.

10. The device of claim 1, wherein the fluidic oscillator is unidirectional or bi-directional.

11. The device of claim 1, where the fluidic oscillator is bidirectional and the at least one obstacle is symmetrical, the device further comprising:
    an inlet nozzle to direct the other portion of the airstream into an oscillation chamber of the fluidic oscillator;
    the symmetrical obstacle within the fluidic oscillator defining a first concave surface and a second concave surface, where the first portion of the airstream contacts the first concave surface in a forward direction to generate forward direction oscillations;
    two or more pathways each defined by the housing and the symmetrical obstacle, wherein the two or more side channels direct the airstream around opposing sides of the symmetrical obstacle after contacting the first concave surface, wherein the two or more side channels further direct the other portion of the airstream to contact the second concave surface in a reverse direction to induce reverse direction oscillations.

12. The device of claim 11 wherein the two or more side channels do not include feedback channels or loops.

13. The device of claim 11, wherein the at least one sensor is proximal to the first concave surface and at least one other sensor proximal to the second concave surface.

14. The device of claim 11, wherein the at least one sensor detects oscillations in both the forward and reverse direction.

15. The device of claim 1, where the fluidic oscillator is bidirectional and the device further comprising:
    another fluidic oscillator having at least one second obstacle, to induce oscillations in the airstream in a reverse direction;
    wherein the fluidic oscillator and the other fluidic oscillator are arranged in a stacked configuration.

16. The device of claim 12, further comprising another nozzle, the other nozzle having at least one reverse channel to vent a reverse portion of the airstream entering the other fluidic oscillator into the environment external to the device and at least one other reverse channel to direct another reverse portion of the airstream into a fluidic oscillator.

17. The device of claim 1, wherein the at least one sensor is selected from a group consisting of a pressure sensor, a piezoelectric sensor, a microphone, and a thermal sensor.

18. The device of claim 1, wherein the at least one channel vents the portion of the airstream into the environment external to the device after entering the device and bypassing the fluidic oscillator.

* * * * *